United States Patent
Mitragotri et al.

(10) Patent No.: US 12,414,999 B2
(45) Date of Patent: Sep. 16, 2025

(54) COMPOSITIONS AND METHODS RELATING TO MACROPHAGES AND/OR MONOCYTES WITH ADHERED PARTICLES

(71) Applicants: PRESIDENT AND FELLOWS OF HARVARD COLLEGE, Cambridge, MA (US); The Regents of the University of California, Oakland, CA (US)

(72) Inventors: Samir Mitragotri, Lexington, MA (US); Michael Andrew Evans, Cambridge, MA (US); Charles Wyatt Shields, IV, Longmont, CO (US)

(73) Assignees: PRESIDENT AND FELLOWS OF HARVARD COLLEGE, Cambridge, MA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 406 days.

(21) Appl. No.: 16/960,393

(22) PCT Filed: Jan. 8, 2019

(86) PCT No.: PCT/US2019/012673
§ 371 (c)(1),
(2) Date: Jul. 7, 2020

(87) PCT Pub. No.: WO2019/139892
PCT Pub. Date: Jul. 18, 2019

(65) Prior Publication Data
US 2020/0376137 A1    Dec. 3, 2020

Related U.S. Application Data

(60) Provisional application No. 62/634,267, filed on Feb. 23, 2018, provisional application No. 62/616,519, filed on Jan. 12, 2018.

(51) Int. Cl.
| | |
|---|---|
| *A61K 47/69* | (2017.01) |
| *A61K 9/51* | (2006.01) |
| *A61K 38/20* | (2006.01) |
| *A61K 38/21* | (2006.01) |
| *A61K 40/17* | (2025.01) |
| *A61K 40/24* | (2025.01) |
| *A61K 40/42* | (2025.01) |
| *A61P 35/00* | (2006.01) |

(52) U.S. Cl.
CPC ........ *A61K 47/6901* (2017.08); *A61K 9/5138* (2013.01); *A61K 9/5153* (2013.01); *A61K 9/5161* (2013.01); *A61K 9/5169* (2013.01); *A61K 38/2026* (2013.01); *A61K 38/217* (2013.01); *A61K 40/17* (2025.01); *A61K 40/24* (2025.01); *A61K 40/42* (2025.01); *A61P 35/00* (2018.01); *A61K 2239/49* (2023.05)

(58) Field of Classification Search
CPC .............. A61K 47/6901; A61K 9/5138; A61K 9/5153; A61K 9/5161; A61K 9/5169; A61K 38/2026; A61K 38/217; A61K 40/17; A61K 40/24; A61K 40/42; A61K 2239/49; A61K 31/728; A61K 38/191; A61K 38/193; A61K 38/20; A61K 38/204; A61K 38/208; A61K 45/06; A61K 38/19; A61P 35/00; A61P 17/02
See application file for complete search history.

(56) References Cited

U.S. PATENT DOCUMENTS

| | | | |
|---|---|---|---|
| 6,355,270 B1* | 3/2002 | Ferrari ................ | A61K 9/0097 514/10.9 |
| 6,998,393 B2 | 2/2006 | Jin et al. | |
| 2009/0258057 A1 | 10/2009 | Swiston et al. | |
| 2011/0038939 A1* | 2/2011 | Lvov .................... | A61K 9/5138 424/490 |
| 2012/0195939 A1* | 8/2012 | Nadal-Ginard ...... | A61K 9/1605 514/8.4 |
| 2013/0045162 A1* | 2/2013 | Lillard, Jr. ............. | A61P 35/00 977/773 |
| 2015/0010630 A1 | 1/2015 | Llamas et al. | |
| 2016/0331802 A1 | 11/2016 | Li et al. | |
| 2017/0266317 A1 | 9/2017 | Polak et al. | |
| 2018/0243440 A1 | 8/2018 | Muzykantov et al. | |

FOREIGN PATENT DOCUMENTS

| | | |
|---|---|---|
| WO | 2004032970 A2 | 4/2004 |
| WO | 2009134866 A2 | 11/2009 |

OTHER PUBLICATIONS

Shields et al. "Induction of lymphoidlike stroma and immune escape by tumors that express the chemokine CCL21." Science 328.5979 (2010): 749-752.

(Continued)

*Primary Examiner* — Robert S Cabral
(74) *Attorney, Agent, or Firm* — NIXON PEABODY LLP; David S. Resnick; Nicole D. Kling

(57) ABSTRACT

Provided herein are polymeric particles and compositions (i.e., "backpacks") that can adhere to cells and provide delivery of payload immunomodulatory agents to those cells. For examples, the particles can adhere to macrophages and/or monocytes and release cytokines that promote an M1 or M2 phenotype to improve therapeutic efficacy of the cells.

21 Claims, 16 Drawing Sheets

(56) References Cited

OTHER PUBLICATIONS

Guo et al. "Modular assembly of superstructures from polyphenol-functionalized building blocks." Nature Nanotechnology 11(12): 1105-1111 (2016).

Von Staszewski et al. "Nanocomplex formation between β-lactoglobulin or caseinomacropeptide and green tea polyphenols: Impact on protein gelation and polyphenols antiproliferative activity." Journal of Functional Foods 4(4): 800-809 (2012).

Ma "Establishment and in vitro evaluation of CPT-11-PLGA nanoparticle erythrocyte system", pp. 15-25, Published date: Mar. 15, 2017 [English Translation Provided].

Anselmo et al., "Cell-mediated delivery of nanoparticles: taking advantage of circulatory cells to target nanoparticles." Journal of Controlled Release 190:531-541 (2014).

Anselmo et al., "Monocyte-mediated delivery of polymeric backpacks to inflamed tissues: a generalized strategy to deliver drugs to treat inflammation." Journal of Controlled Release 199:29-36 (2015).

Ayer et al., "Cell-mediated delivery of synthetic nano-and microparticles." Journal of Controlled Release 259:92-104 (2017).

Villa et al., "Red blood cells: supercarriers for drugs, biologicals, and nanoparticles and inspiration for advanced delivery systems." Advanced Drug Delivery Reviews 106:88-103 (2016).

Anselmo et al., "Delivering Nanoparticles to Lungs while Avoiding Liver and Spleen through Adsorption on Red Blood Cells" ACS Nano 7(12):11129-11137 (2013).

Chu et al. "Photosensitization Priming of Tumor Microenvironments Improves Delivery of Nanotherapeutics via Neutrophil Infiltration" Advanced Materials 29:1701021 (2017).

Fahmy et al. "Nanosystems for Simultaneous Imaging and Drug Delivery to T Cells" The AAPS Journal 9:19 (2007).

Park et al. "Hyaluronic acid-coated nanparticles for targeted photodynamic theapy of cancer guided by near-infrared and MR imaging." Carbohydrate Polymers 157:476-483 (2016).

Steenblock et al. "An Artificial Antigen-presenting Cell with Pracrine Delivery of IL-2 Impacts the Magnitude and Direction of the T Cell Reponse." TBC 40:34883-34592 (2011).

Tang et al. "Enhancing T cell therapy through TCR signaling-responsive nanoparticle drug delivery" Nat Biotechnol 36:707-716 (2018).

Warren et al. "A novel binding assy to assess specificity of monoclonal antibodies." J Immunol Methods 305:33-38 (2005).

Zhang et al. "Hyaluronic Acid-Chitosan Nanoparticles to Deliver Gd-DTPA for MR Cancer Imaging." Nanomaterials 5:1379-1396 (2015).

Seo et al. "Effect of the Layer-by-Layer (LbL) Deposition Method on the Surface Morphology and Wetting Behavior of Hydrophobically Modified PEO and PAA LbL Films." Langmuir 24:7995-8000 (2008).

Hammond et al. "Engineering Materials Layer-by-Layer: Challenges and Opportunities in Multilayer Assembly." AIChE Journal 57(11) 2928-2940 (2011).

Pan et al. "Nanoparticle properties modulate their attachment and effect on carrier red blood cells." Scientific Reports 8.1: 1615 (2018).

Kapoor et al. "PLGA: a unique polymer for drug delivery." Therapeutic delivery 6.1: 41-58 (2015).

Luk et al. "Safe and immunocompatible nanocarriers cloaked in RBC membranes for drug delivery to treat solid tumors." Theranostics 6.7: 1004-1011 (2016).

Steenblock et al. "A Comprehensive Platform for Ex Vivo T-cell Expansion Based on Biodegradable Polymeric Artificial Antigen-presenting Cells." Molecular Therapy 16(4):765-772 (2008).

* cited by examiner

COMPOSITIONS AND METHODS RELATING TO MACROPHAGES AND/OR MONOCYTES WITH ADHERED PARTICLES

CROSS-REFERENCE TO RELATED APPLICATIONS

This application is a 35 U.S.C. § 371 National Phase Entry Application of International Application No. PCT/US2019/012673 filed Jan. 8, 2019, which designates the U.S. and claims benefit under 35 U.S.C. § 119 (e) of U.S. Provisional Application Nos. 62/616,519 filed Jan. 12, 2018 and 62/634,267 filed Feb. 23, 2018, the contents of which are incorporated herein by reference in their entireties.

TECHNICAL FIELD

The technology described herein relates to methods and compositions relating to macrophages and/or monocytes with particles adhered to their cell surface.

BACKGROUND

Adoptive T-cell therapies have shown great therapeutic promise. Adoptive macrophage therapy has the potential to provide an equally efficacious therapeutic approach with even greater flexibility and broader applications. However, attempts at adoptive macrophage therapy to date have failed, as the macrophages tend to quickly lose the desired phenotype.

SUMMARY

Described herein is an approach which permits a macrophage to retain a desired phenotype without comprising the activity or mobility of the cell or genetically modifying the cell itself. This approach relies upon polymeric particles on the cell surface (also referred to herein as "backpacks"). These polymeric particles are phagocytosis-resistant and comprise polarizing agents which can regulate the cell's phenotype. Thus, attaching the polymeric particle to the cell surface causes the cell to assume the desired phenotype (e.g., M1 or M2, generally corresponding to pro-inflammatory and anti-inflammatory phenotypes) and retain it for a sustained period, e.g, until the polymeric particle is released from the cell surface. As demonstrated herein, this permits effective adoptive macrophage therapy.

In one aspect of any of the embodiments, described herein is an engineered cellular composition comprising:
 a. a monocyte or macrophage cell; and
 b. a polymeric particle comprising at least one polarizing agent, wherein the particle is located on the cell surface of the monocyte or macrophage.

In one aspect of any of the embodiments, described herein is an engineered cellular composition comprising:
 a. a monocyte or macrophage cell; and
 b. a polymeric particle comprising at least one M1-polarizing agent or at least one M2-polarizing agent, wherein the particle is located on the cell surface of the monocyte or macrophage.

In some embodiments of any of the aspects, the cell is a monocyte. In some embodiments of any of the aspects, the cell is a macrophage. In some embodiments of any of the aspects, the macrophage is an M1 macrophage. In some embodiments of any of the aspects, the macrophage is an M2 macrophage. In some embodiments of any of the aspects, the macrophage is an M1-polarized macrophage. In some embodiments of any of the aspects, the macrophage is an M2-polarized macrophage. In some embodiments of any of the aspects, the macrophage is substantially driven to an M1 or M2 phenotype. In some embodiments of any of the aspects, the macrophage has an M0 polarization and is substantially driven to an M1 or M2 phenotype.

In one aspect of any of the embodiments, described herein is a polymeric particle comprising at least one polarizing agent. In one aspect of any of the embodiments, described herein is a polymeric particle comprising at least one M1-polarizing agent and at least one M2-polarizing agent. In one aspect of any of the embodiments, described herein is a polymeric particle comprising at least one M1-polarizing agent or at least one M2-polarizing agent. In one aspect of any of the embodiments, described herein is a polymeric particle comprising at least one polarizing agent and
 a. a first region comprising one or more cell adhesive molecules (e.g., polyelectrolytes);
 b. a second region comprising one or more structural polymers.

In some embodiments of any of the aspects, the polarizing agent is an M1-polarizing agent. In some embodiments of any of the aspects, the polarizing agent is an M2-polarizing agent. In some embodiments of any of the aspects, the M1-polarizing agent is selected from the group consisting of: IFN-γ; TNF; a Toll-like receptor agonist; IL-12; and IL-23. In some embodiments of any of the aspects, the M1-polarizing agent is selected from the group consisting of: IFN-γ; TNF; TNF-alpha; a Toll-like receptor agonist (e.g., LPS, muramyl dipeptide, or lipoteichoic acid); GM-CSF; IL-1β; IL-6; IL-12; IL-23, and CD11b. In some embodiments of any of the aspects, the M2-polarizing cytokine polypeptide is selected from the group consisting of: IL-4; IL-10; glucocortoids (e.g., cortisol, cortisone, prednisone, prednisolone, methylprednisonolone, dexamethasone, betamethasone, triamcinolone, fludrocortisone acetate, and deoxycorticosterone acetate); M-CSF, TGF-beta, IL-6; and IL-13.

In some embodiments of any of the aspects, the polymeric particle is substantially discoidal in shape. In some embodiments of any of the aspects, the polymeric particle is discoidal in shape. In some embodiments of any of the aspects, the polymeric particle has a shape which is a rod, a cylinder, a cube, a cuboid, a hexahedron, or a pyramid. In some embodiments of any of the aspects, the diameter of the polymeric particle is from about 100 nm to about 10 μm. In some embodiments of any of the aspects, the polymeric particle is about 6 μm×250 nm in size. In some embodiments of any of the aspects, the polymeric particle is about 6 μm×500 nm in size.

In some embodiments of any of the aspects, the polymeric particle comprises:
 a. a first region comprising one or more cell adhesive molecules (e.g., polyelectrolytes);
 b. a second region comprising one or more structural polymers.

In some embodiments of any of the aspects, the cell adhesive molecules comprise one or more of cell adhesive polyelectrolytes, immunoglobulins, or ligands for receptors on monocyte or macrophage cell surfaces. In some embodiments of any of the aspects, the cell adhesive polyelectrolytes comprise hyaluronic acid and/or poly(allylamine) hydrochloride. In some embodiments of any of the aspects, the hyaluronic acid is modified to comprise aldehyde groups.

In some embodiments of any of the aspects, the structural polymer comprises poly(lactic-co-glycolic) acid (PLGA) or poly(glycerol sebacate) (PGS). In some embodiments of any of the aspects, the structural polymer comprises poly(lactic-co-glycolic) acid (PLGA), polyvinyl alcohol (PVA), hyaluronic acid (HA), gelatin, alginate, collagen, fibronechtin, polycapralactone, chitosan or poly(glycerol sebacate) (PGS). In some embodiments of any of the aspects, the structural polymer is a 1-20 wt. % solution of the structural polymer. In some embodiments of any of the aspects, the structural polymer is a 5-20 wt. % solution of the structural polymer. In some embodiments of any of the aspects, the structural polymer is a 10 wt. % solution of the structural polymer.

In some embodiments of any of the aspects, the second region further comprises poly(lactic-co-caprolactone) (PLCL). In some embodiments of any of the aspects, the second region comprises or further comprises a near-infrared degradable, or biologically degradeable polymer or polymer linker.

In some embodiments of any of the aspects, the polymeric particle further comprises one or more monocyte-targeting and/or macrophage-targeting ligands. In some embodiments of any of the aspects, the monocyte-targeting and/or macrophage-targeting ligand is located in the region comprising cell adhesive molecules (e.g., polyelectrolytes). In some embodiments of any of the aspects, the monocyte-targeting and/or macrophage-targeting ligand is IgG, an antibody, a polypeptide, or an aptamer.

In some embodiments of any of the aspects, the polymeric particle further comprises one or more payload molecules. In some embodiments of any of the aspects, the payload molecule is a small molecule or polypeptide. In some embodiments of any of the aspects, the payload molecule is present in admixture with the structural polymer. In some embodiments of any of the aspects, the payload molecule is present in a third region of the polymeric particle which is located between the first and second regions.

In some embodiments of any of the aspects, the polymeric particle further comprises an echogenic liposome. In some embodiments of any of the aspects, the polymeric particle further comprises a magnetic nanoparticle. In some embodiments of any of the aspects, the polymeric particle further comprises a gold nanoparticle.

In some embodiments of any of the aspects, a region is a layer.

In some embodiments of any of the aspects, the release of one or more of the polarizing agents is triggered by contacting the particle with a small molecule or nucleic acid. In some embodiments of any of the aspects, the phenotype of the macrophage is regulated by the release of the one or more polarizing agents.

In one aspect of any of the embodiments, described herein is a method of treating cancer and/or a tumor in a subject in need thereof, the method comprising administering to the subject the engineered cellular composition described herein. In some embodiments of any of the aspects, the method further comprises administering radiation or at least one chemotherapy to the subject.

In one aspect of any of the embodiments, described herein is a method of treating a fracture, wound, or infection in a subject in need thereof, the method comprising administering to the subject the engineered cellular composition as described herein. In one aspect of any of the embodiments, described herein is a method of treating inflammation in a subject in need thereof, the method comprising administering to the subject the engineered cellular composition described herein. In some embodiments of any of the aspects, the inflammation is in the lungs arising from infection or injury. In some embodiments of any of the aspects, the inflammation is in a joints and is caused by or arises from arthritis. In some embodiments of any of the aspects, the inflammation is in the skin and arises from or is caused by infection or autoimmune disease. In some embodiments of any of the aspects, the inflammation is, is caused by, or is a symptom of acute respiratory distress syndrome (ARDS), arthritis, infection, or autoimmune disease.

In some embodiments of any of the aspects, the polymeric particle comprises IL-4. In some embodiments of any of the aspects, the cell is autologous to the subject. In some embodiments of any of the aspects, the cell is heterologous to the subject. In some embodiments of any of the aspects, the method further comprises a first step of obtaining the cell from a donor and/or the subject and contacting the cell with the polymeric particle ex vivo. In some embodiments of any of the aspects, a therapeutically effective dose of the composition is administered.

In some embodiments of any of the aspects, the second region of the polymeric particle comprises poly(lactic-co-caprolactone) (PLCL) and the method further comprises increasing the temperature of at least one area of the subject in order to permit the cell to phagocytose the polymeric particles. In some embodiments of any of the aspects, the second region of the polymeric particle comprises a near-infrared degradable polymer or polymer linker and the method further comprises subject at least one area of the subject to near-infrared light in order to permit the cell to phagocytose the polymeric particles. In some embodiments of any of the aspects, the polymeric particle comprises an echogenic liposome and the method further comprises subject at least one area of the subject to ultrasound in order to permit the cell to phagocytose the polymeric particles or to release a payload molecule. In some embodiments of any of the aspects, the polymeric particle comprises a magnetic nanoparticle and the method further comprises subject at least one area of the subject to a magnetic field in order to permit the cell to phagocytose the polymeric particles or to release a payload molecule. In some embodiments of any of the aspects, the polymeric particle comprises a gold nanoparticle and the method further comprises subject at least one area of the subject to an electromagnetic wave in order to permit the cell to phagocytose the polymeric particles or to release a payload molecule.

In one aspect of any of the embodiments, described herein is a method of producing a polymeric particle described herein, the method comprising:
a. applying a layer-by-layer coating of one or more cell adhesive molecules (e.g., polyelectrolytes) to a stamp, e.g., with micropatterned features made by soft lithography to form the first region;
b. applying the one or more structural polymers to the stamp with a spin coater to form the second region;
c. printing the resulting two regions onto a surface coated with poly(vinyl alcohol) (PVA) and peeling away the stamp; and
d. contacting the product of step c with an aqueous solution to release the polymeric particles.

In some embodiments of any of the aspects, the stamp comprises circular columns. In some embodiments of any of the aspects, the stamp is a polydimethylsiloxane (PDMS) stamp. In some embodiments of any of the aspects, the one or more structural polymers are applied as a solution. In some embodiments of any of the aspects, the one or more structural polymers are applied as a solution in acetone. In some embodiments of any of the aspects, the PVA on the surface has been exposed to water vapor prior to step c.

BRIEF DESCRIPTION OF THE DRAWINGS

FIG. 7A depicts AFM analysis. FIG. 7B depicts measurement of physical properties and printing efficiency.

DETAILED DESCRIPTION

Figure 1:
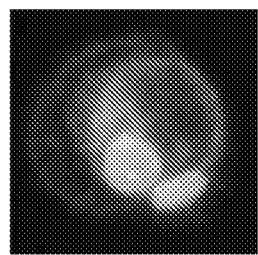
FIG. 1 depicts a confocal image of a monocyte with attached cell backpacks. Backpacks attach to cells without compromising cell function.
Figure 2:
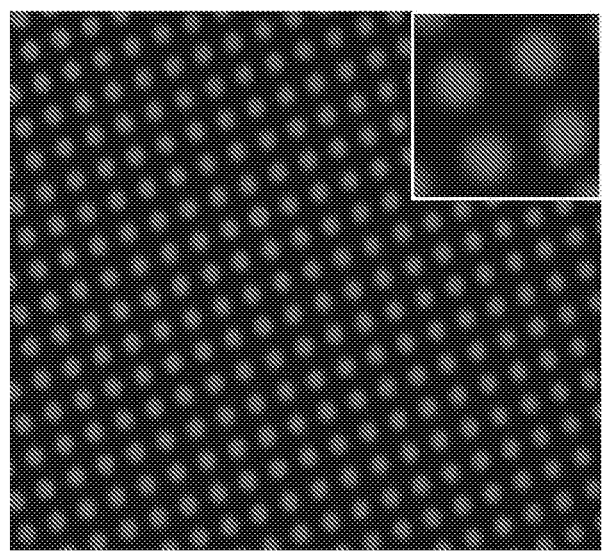
FIG. 2 depicts synthesis of backpacks (labeled by rhodamine) using microcontact printing.

The methods and compositions described herein relate to polymeric particles which can be adhered to a cell surface, e.g., the surface of a monocyte or macrophage. These polymeric particles comprise at least one polarizing agent. When the polymeric particles described herein are adhered to a cell surface, they are resistant to phagocytosis, but able to regulate the phenotype of the cell via the polarizing agent(s). Thus, the polymeric particles permit persistence of the desired cell phenotype, e.g., for therapeutic purposes. In one aspect of any of the embodiments, described herein is a polymeric particle comprising at least one polarizing agent.

In one aspect of any of the embodiments, described herein is an engineered cellular composition comprising: a) a monocyte or macrophage cell; and b) a polymeric particle comprising at least one polarizing agent, wherein the particle is located on the cell surface of the monocyte or macrophage. Described herein are cells, e.g., macrophages and/or monocytes with adhered particles which are referred to interchangeably herein as "adhered particles", "polymeric particles" or "backpacks." In some embodiments of any of the aspects, the cell is a monocyte cell. In some embodiments of any of the aspects the cell is a monocyte cell at the time the polymeric particle is adhered to the cell (e.g., the cell, either under the influence of the particle, or independently thereof, may differentiate to a macrophage after adherence). In some embodiments of any of the aspects, the cell is a macrophage cell, e.g., an M0, M1, M2, M1-polarized, or M2-polarized macrophage.

The presence of the polymeric particle on the surface of the cell can, by contacting the cell with the polarizing agent, direct or regulate the phenotype of the cell, e.g., increase the likelihood, duration, magnitude, or rate of development M1 or M2 phenotypic characteristics. In some embodiments of any of the aspects, the macrophage is substantially driven to an M1 or M2 phenotype by adherence of the polymeric particle. In some embodiments of any of the aspects, the phenotype of the macrophage is regulated by the release of the one or more polarizing agent from the polymeric particle, e.g., induced or non-induced release of the cytokine and/or induced or non-induced degradation of the polymeric particle.

An M1 or M1-polarized macrophage, also referred to as "killer" macrophages, promote inflammation and have anti-tumor activity. They secrete high levels of IL-12 and low levels of IL-10. M1 macrophages can be characterized by the expression of, e.g., CCL3, CCL5, CD80, CCR7, iNOS and INF-γ. An M2 or M2-polarized macrophage, also referred to as a "repair" macrophage, contributes to wound healing and tissue repair. M2 macrophages can suppress the immune system and/or inflammation, e.g., by producing high levels of IL-10. An M2-polarized macrophage can be characterized by the expression of, e.g., CCL22, CD206, CD163, YM1, Fizz1, and arginase 1.

As described herein, a "polarizing agent" is an agent, that when contacted with a macrophage and/or monocyte, alters the likelihood, persistence, magnitude, or rate of development of a particular macrophage phenotype (e.g., either M1 or M2 phenotype) as compared to the absence of the polarizing agent. A polarizing agent can be an M1-polarizing agent, e.g., it increases the likelihood, persistence, or rate of development of an M1 phenotype, or an M2-polarizing agent, e.g., it increases the likelihood, persistence, or rate of development of an M2 phenotype. Exemplary M1 and M2 phenotypes are described herein and are well known in the art. Further details can be found, e.g., in Mills et al. "M1/M2 macrophages" *Frontiers Media SA* (2015) and Kloc "Macrophages: Origin, Function, and Biointervention" *Spring* (2017); each of which are incorporated by reference herein in their entireties.

Polarizing agents for the M1 and M2 macrophage phenotypes are known in the art, and can include, by way of non-limiting example, the M1-polarizing Toll-like receptor (TLR) agonists (e.g., LPS, muramyl dipeptide, or lipoteichoic acid); the M1-polarizing cytokines IFN-γ (e.g., NCBI Gene ID: 3458); TNF (e.g., NCBI Gene ID: 7124); IL-12 (e.g., NCBI Gene ID: 3592 and 3593); GM-CSF (e.g., NCBI Gene ID: 1438); IL-1β (e.g., NCBI Gene ID: 3553); IL-6 (e.g., NCBI Gene ID: 3569); CD11b (e.g., NCBI Gene ID: 3684) and IL-23 (e.g., NCBI Gene ID: 51561) and the M2-polarizing cytokines IL-4 (e.g., NCBI Gene ID: 3565); IL-10 (e.g., NCBI Gene ID: 3586); glucocortoids (e.g., cortisol, cortisone, prednisone, prednisolone, methylprednisonolone, dexamethasone, betamethasone, triamcinolone, fludrocortisone acetate, and deoxycorticosterone acetate); M-CSF (e.g., NCBI Gene ID: 1435), TGF-beta (e.g. NCBI Gene ID: 7040); IL-6 (e.g., NCBI Gene ID: 3569); and IL-13 (e.g., NCBI Gene ID: 3596). TLR agonists are known in the art and can include, by way of non-limiting example LPS, dsRNA; flagella; bacterial lipoprotein; ssRNA; cpG DNA; bacterial peptidoglycans; profillin; rRNA; imiquimod; resiquimod; IMO-2055; picibanil; monophsophoryl lipid A (MPL); polyribocytidylic acid (polyI:C); CpG-28; MGN1703; glucopyranosyl lipid A; entolimod; and ODN2006. Further details on TLR agonists can be found, e.g., in Kaczanowska et al. 2013 *J. Leukoc. Biol.* 93:847-863; which is incorporated by reference herein in its entirety. TLR agonists are also available commercially, e.g., TLR1-9 Agonist Kit (Cat. No. tlrl-kit1hw; Invitrogen; San Diego, CA).

In some embodiments of any of the aspects, the polymeric particle described herein comprises a first region comprising one or more cell adhesive molecules; and a second region comprising one or more structural polymers. In some embodiments of any of the aspects, a region can be a layer. In some embodiments of any of the aspects, a region can be a face of the discoidal shape of the particle. In some embodiments of any of the aspects, the second or third region can be the interior space (or a portion thereof) of the discoidal shape of the particle.

The polarizing agent(s) can be present in the first region, the second region, a third region forming layer in between the first and second regions, in the interior space of the polymeric particle, or any combination thereof. In some embodiments of any of the aspects, the third region can comprise a different structural polymer or mixture of structural polymers than the first and third regions.

In some embodiments of any of the aspects, the third region comprises PVA. In some embodiments of any of the aspects, the third region consists essentially of PVA and the payload molecule(s). In some embodiments of any of the aspects the PVA is present at a concentration of less than 1% by weight. In some embodiments of any of the aspects the PVA is present at a concentration of 0.5% or less by weight. Placement of the polarizing agent can be influenced by whether the polarizing effect should be exerted immediately following adherence of the particle, or if it is desired to induce the polarizing effect by controlled degradation of the polymeric particle as described below herein. In some embodiments of any of the aspects, the polarizing agent can be present in the first region. In some embodiments of any of the aspects, the first region comprises the polarizing agent. In some embodiments of any of the aspects, only the first region comprises the polarizing agent.

Cell adhesive molecules can be any molecule which will adhere to the surface of a cell, e.g., a monocyte or macrophage cell. Non-limiting examples of suitable cell adhesive molecules include polyelectrolytes, immunoglobulins, ligands for receptors on a cell surface, and/or monocyte-targeting and/or macrophage-targeting ligands. Characteristics that can enhance cell adhesion include, e.g., high surface free energy, hydrophilic protein content, low surface hydration, and low surface charge density. Exemplary, non-limiting cell adhesive molecules can include poly(glycidyl methacrylate) (PGMA); polycaprolactone (PCL); polydimethylsiloxane (PDMS); poly(hexamethyldisiloxane) (PHMDSO); superhydrophobic perfluoro-substituted PEDOT (PEDOT-F); superhydrophobic polystyrene (PS); plasma-treated poly(methyl methacrylate) (PMMA); plasma-treated poly-3-hydroxybutyrate (P3HB); phosphatidylethanolamine (PE); and carboxymethyl chitin (CMCH). Cell adhesive molecules can also include, or comprise, e.g., RGD peptides, collagen, fibronectin, gelatin, and collagen. Further discussion of cell adhesive molecules can be found, e.g., at Lih et al. Progress in *Polymer Science* 44:28-61 (2015) and Chen et al. *Materials Today* (2017); which are incorporated by reference herein in their entireties.

In some embodiments of any of the aspects, cell adhesive polyelectrolytes comprise hyaluronic acid, poly(allylamine) hydrochloride, and/or hyaluronic acid modified to comprise aldehyde groups.

Ligands for the receptors on a given cell surface and/or which target a monocyte or macrophage are known in the art and can include natural or synthetic ligands. Exemplary ligands for macrophages and/or monocytes can include, by way of non-limiting example, IL-4; CX3CL1; IL-17A; IL-17F; M-CSF; GM-CSF; LDL; ApoE; IL-2; IFN-γ; Hsp60; Hsp70; complement CSA; leukotriene B4; CCL2; CCL4; CCL3; CCL5; CCL7; CCL8; CXCL8; CXCL9; CXCL10; and/or CXCL11. In some embodiments of any of the aspects, monocyte-targeting and/or macrophage-targeting ligand is IgG, an antibody (e.g., an antibody specific for a molecule (e.g., a receptor) on the monocyte or macrophage cell surface), a polypeptide, or an aptamer.

In some embodiments of any of the aspects, the cell adhesive molecules can be specific for one or more cell types, e.g., macrophages and/or monocytes. However, the particles can be adhered to isolated cell populations in vitro, and thus such specificity is not required in all embodiments. In some embodiments of any of the aspects, the cell adhesive molecules are not specific for macrophages and/or monocytes.

In some embodiments of any of the aspects, the first region comprises a single type of cell adhesive molecule. In some embodiments of any of the aspects the first region comprises two or more types of cell adhesive molecules, e.g., two cell adhesive polyelectrolytes and/or a cell adhesive polyelectrolyte and an immunoglobulin.

Structural polymers are preferably those which are suitable for forming into a thin disk. Exemplary structural polymers can include, by way of non-limiting example polylactide (PLA): polyglycolide (PGA); poly-(ε-caprolactone) (PCL); polyphosphazenes; polyorthoesters; polyanhydrides; poly(α-hydroxy esters); poly(ether esters); copolymers comprising lactide of glycolide and ε-caprolactone or trimethylene carbonate; poly(polyol sebacate) elastomers; elastomers; poly(polyol citrate); polyesters; poly(glycolic acid); poly(lactic acid); poly(caprolactone); poly(lactic-co-glycolic acid); poly(butylene succinate); poly(trimethylene carbonate); poly(p-dioxanone); poly(butylene terephthalate); poly(ester amide)s; Hybrane™ S1200; DegraPol™; polyurethanes; polyanhydrides; poly[(caboxyphenoxy) propane-sebacic acid]; polyphsophoesters; poly[bis(hydroxyethyl) terephthalate-ethyl orthophosphorylate/terephthaloyl chloride]; poly(ortho esters); poly(alkyl cyanoacrylates); poly(butyl cyanoacrylate); polyethers; poly(ethylene glycol); poly(amino acids); tyrosine derived polycarbonate; microbial polyesters; poly(β-hydroxyalkanoate); poly(hydroxybutyrate); poly(hydroxybutyrate-co-hydroxyvalerate); collagen; albumin; gluten; chitosan; hyaluronate; cellulose; alginate; and starch. Suitable structural polymers are discussed in more detail at, e.g., Bat et al. *Regen. Med.* 9:385-398 (2014) and Marin et al. *Int. J. Nanomedicine* 8:3071-3091 (2013); which are incorporated by reference herein in their entireties. In some embodiments of any of the aspects, the structural polymer comprises poly(lactic-co-glycolic) acid (PLGA), polyvinyl alcohol (PVA), hyaluronic acid (HA), gelatin, collagen and/or poly(glycerol sebacate) (PGS).

In some embodiments of any of the aspects, the second region comprises a single structural polymer. In some embodiments of any of the aspects the second region comprises two or more structural polymers.

In some embodiments of any of the aspects, the second region further comprises poly(lactic-co-caprolactone) (PLCL). In some embodiments of any of the aspects, the second region comprises a) poly(lactic-co-glycolic) acid (PLGA) and/or poly(glycerol sebacate) (PGS) and b) poly (lactic-co-caprolactone) (PLCL).

In some embodiments of any of the aspects, the second region is, or is formed using, an about 5-20 wt. % solution of the structural polymer. In some embodiments of any of the aspects, the second region is, or is formed using, a 5-20 wt. % solution of the structural polymer. In some embodiments of any of the aspects, the second region is, or is formed using, an about 1-20 wt. % solution of the structural polymer. In some embodiments of any of the aspects, the second region is, or is formed using, a 1-20 wt. % solution of the structural polymer. In some embodiments of any of the aspects, the second region is, or is formed using, an about 8-12 wt. % solution of the structural polymer. In some embodiments of any of the aspects, the second region is, or is formed using, an 8-12 wt. % solution of the structural polymer.

In some embodiments of any of the aspects, the second region is, or is formed using, an about 10 wt. % solution of the structural polymer. In some embodiments of any of the aspects, the second region is, or is formed using, a 10 wt. % solution of the structural polymer.

As described in the examples herein, discoidal particles displayed favorable characteristics, e.g., for being retained on the cell surface without altering the cell's behavior. In some embodiments of any of the aspects, the polymeric particle is substantially discoidal in shape. In some embodiments of any of the aspects, the polymeric particle is discoidal in shape. As used herein, "discoidal" refers to a particle having a disk-like shape, with substantially flat, concave or convex faces.

In some embodiments of any of the aspects, a polymeric particle described herein has a disk-like shape, wherein the diameter of the circular face(s) is from about 4× to about 35× the size of the height (e.g., or depth) of the particle. In some embodiments of any of the aspects, a polymeric particle as described herein has a disk-like shape, wherein the diameter of the circular face(s) is from 4× to 35× the size of the height of the particle. In some embodiments of any of the aspects, a polymeric particle as described herein has a disk-like shape, wherein the diameter of the circular face(s) is from about 10× to about 35× the size of the height (e.g., or depth) of the particle. In some embodiments of any of the aspects, a polymeric particle as described herein has a disk-like shape, wherein the diameter of the circular face(s) is from 10× to 35× the size of the height of the particle. In some embodiments of any of the aspects, a polymeric particle as described herein has a disk-like shape, wherein the diameter of the circular face(s) is from about 18× to about 26× the size of the height of the particle. In some embodiments of any of the aspects, a polymeric particle as described herein has a disk-like shape, wherein the diameter of the circular face(s) is from 18× to 26× the size of the height of the particle.

In some embodiments of any of the aspects, a substantially discoidal particle has two substantially opposing and circular faces and the diameter of each face is at least 10× the height (e.g., depth) of the particle. In some embodiments of any of the aspects, a substantially circular face's widest diameter is no more than 150% of the shortest diameter of that face.

In some embodiments of any of the aspects, the polymeric particle has a shape which is a rod, a cylinder, a cube, cuboid, hexahedron, or pyramid.

In some embodiments of any of the aspects, the diameter of the polymeric particle is from about 50 nm to about 20 µm. In some embodiments of any of the aspects, the diameter of the polymeric particle is from 50 nm to 20 µm. In some embodiments of any of the aspects, the diameter of the polymeric particle is from about 100 nm to about 10 µm. In some embodiments of any of the aspects, the diameter of the polymeric particle is from 100 nm to 10 µm. In some embodiments of any of the aspects, the diameter of the polymeric particle is from about 1 µm to about 10 µm. In some embodiments of any of the aspects, the diameter of the polymeric particle is from 1 µm to 10 µm.

In some embodiments of any of the aspects, the polymeric particle is about 3 µm×150 nm in size to about 12 µm×500 nm in size. In some embodiments of any of the aspects, the polymeric particle is 3 µm×150 nm in size to 12 µm×500 nm in size. In some embodiments of any of the aspects, the polymeric particle is about 6 µm×500 nm in size. In some embodiments of any of the aspects, the polymeric particle is 6 µm×500 nm in size. In some embodiments of any of the aspects, the polymeric particle is about 6 µm×250 nm in size. In some embodiments of any of the aspects, the polymeric particle is 6 µm×250 nm in size.

In some embodiments of any of the aspects, the polymeric particle is about 0.5-5 µm×5-15 µm in size. In some embodiments of any of the aspects, the polymeric particle is 0.5-5 µm×5-15 µm in size. In some embodiments of any of the aspects, the polymeric particle is about 1-2 µm×7-9 µm in size. In some embodiments of any of the aspects, the polymeric particle is 1-2 µm×7-9 µm in size. In some embodiments of any of the aspects, the polymeric particle is about 1.5 µm×8 µm in size.

Embodiments of the particles described herein can be controllably-degraded, e.g., either to control delivery of a payload (e.g., temporally or spatially) or to regulate the effect of the particle on the carrier cell (e.g., the monocyte or macrophage). One approach to such controllable-degradation is to utilize particles in which the second region comprises degradable polymers or polymer linkers. In some embodiments of any of the aspects, the particle, e.g., the second region of the particle, comprises or further comprises a near-infrared degradable polymer or near-infrared degradable polymer linker. Non-limiting examples of such near-infrared degradable materials can include those comprising quinone-methide light-sensitive groups, which are described in more detail in Fomina et al. *J. Am. Chem. Soc.* 132:9540-9542; which is incorporated by reference herein in its entirety.

In some embodiments of any of the aspects, the polymeric particle further comprises one or more monocyte-targeting and/or macrophage-targeting ligands. The ligands can be located in the first region, the second region, or in both regions. In some embodiments of any of the aspects, the polymeric particle further comprises one or more further monocyte-targeting and/or macrophage-targeting ligands. In some embodiments of any of the aspects, the polymeric particle further comprises one or more monocyte-targeting and/or macrophage-targeting ligands in the first region. Such targeting ligands can also act as polarizing agents, or may have no effect on the phenotype of the cell, functioning only to increase binding affinity and/or specificity of the particle.

The particles described herein can comprise payload molecules, e.g., therapeutic molecules (e.g., a chemotherapeutic molecule or anti-inflammatory molecule), imaging molecules, or the like. The payload molecule can act on the monocyte or macrophage, or on a second cell/cell type. Payload molecules can be any type of agent. In some embodiments of any of the aspects, the payload molecule is a small molecule or polypeptide.

In some embodiments of any of the aspects, the payload molecule is present in admixture with the structural polymer. In some embodiments of any of the aspects, the payload molecule is present in a third region of the polymeric particle which is located between the first and second regions, e.g., as a layer between the first and second regions, or in the interior space of the particle.

As described herein, certain embodiments of the particles described herein can be disrupted or degraded in a controllable and/or inducible manner. The particles can also be localizable. One approach to providing such functionality is to incorporate into the particle a liposome or nanoparticle that can be disrupted or removed by a controllable external stimulus. For example, echogenic liposomes are known in the art and can be disrupted by certain frequency of sound, e.g., ultrasound waves. For further details, see, e.g., Paul et al. 2014 *Comput. Mech.* 53(3) 413-435; Immordino et al. 2006 *Int. J. Nanomedicine* 1(3):294-315; Nahire et al. 2014 *Mol. Pharmaceutics* 11(11):4059-4068; U.S. Pat. No. 6,261,537; and US Patent Publication 2001/0051131; each of which is incorporated by reference herein in its entirety. Magnetic and gold nanoparticles are responsive to magnetic and electromagnetic fields respectively, and this functionality can be used to localize the particles, localize the cells they are adhered to, and/or to disrupt the particles. Further details of such nanoparticles and their use in such methods can be found, e.g., in Thanh "Magnetic Nanoparticles" 2012 CRC Press; Khan et al. 2015 *Curr. Drug Metab.* 16:685-704; Yeh et al. 2012 *Nanoscale* 6; Sengani et al. 2017 *OpenNano* 2:37-46; and Menon et al. 2017 *Resource-Efficient Technologies* 3:516-527; each of which is incorporated by reference herein its entirety. Further discussion of the foregoing exemplary embodiments and other means of controlled release are described in detail in Mishra "Handbook of Encapsulation and Controlled Release" CRC Press (2015); which is incorporated by reference herein in its entirety. In some embodiments of any of the aspects, foregoing liposomes and/or nanoparticles can be in the second region of the polymeric particle.

In some embodiments of any of the aspects, the release of one or more of the polarizing agents is triggered by contacting the particle with a small molecule or nucleic acid. Exemplary, non-limiting examples of such methods and reagents include particles comprising phenylboronic acid (PBA), which will release cargo in response to insulin. Further details of this approach are described in Shiino et al. *Biomaterials* 15:121-128 (1994); which is incorporated by reference herein in its entirety.

In one aspect of any of the embodiments, described herein is an engineered cellular composition comprising: a cell; and a polymeric particle comprising an M1-polarizing agent, e.g., cytokine polypeptide, wherein the particle is located on the cell surface of the cell. In one aspect of any of the embodiments, described herein is an engineered cellular composition comprising: a monocyte or macrophage cell; and a polymeric particle comprising an M1-polarizing agent, e.g., polarizing cytokine polypeptide, wherein the particle is located on the cell surface of the monocyte or macrophage. In one aspect of any of the embodiments, described herein a polymeric particle comprising an M1-polarizing agent, e.g., a cytokine polypeptide.

In one aspect of any of the embodiments, described herein is an engineered cellular composition comprising: a) a monocyte or macrophage cell; and b) a polymeric particle comprising at least one M1-polarizing cytokine agent and/or at least one M2-polarizing agent, wherein the particle is located on the cell surface of the monocyte or macrophage. In one aspect of any of the embodiments, described herein is an engineered cellular composition comprising: a) a monocyte or macrophage cell; and b) a polymeric particle comprising at least one M1-polarizing cytokine agent or at least one M2-polarizing agent, wherein the particle is located on the cell surface of the monocyte or macrophage.

As used herein, the term "polymer" refers to oligomers, co-oligomers, polymers and copolymers, e.g., random block, multiblock, star, grafted, gradient copolymers and combination thereof. The average molecular weight of the polymer, as determined by gel permeation chromatography, can range from 500 to about 500,000, e.g., from 20,000 to about 500,000. Without limitation, any polymeric material known in the art can be used in the invention. Accordingly, in some embodiments, the polymer is selected from the group consisting of polysaccharides, polypeptides, polynucleotides, copolymers of fumaric/sebacic acid, poloxamers, polylactides, polyglycolides, polycaprolactones, copolymers of polylactic acid and polyglycolic acid, polyanhydrides, polyepsilon caprolactone, polyamides, polyurethanes, polyesteramides, polyorthoesters, polydioxanones, polyacetals, polyketals, polycarbonates, polyorthocarbonates, polydihydropyrans, polyphosphazenes, polyhydroxybutyrates, polyhydroxyvalerates, polyalkylene oxalates, polyalkylene succinates, poly(malic acid), poly (amino acids), polyvinylpyrrolidone, polyethylene glycol, polyhydroxycellulose, polymethyl methacrylate, chitin, chitosan, copolymers of polylactic acid and polyglycolic acid, poly(glycerol sebacate) (PGS), gelatin, collagen, silk, alginate, cellulose, poly-nucleic acids, cellulose acetates (including cellulose diacetate), polyethylene, polypropylene, polybutylene, polyethylene terphthalate (PET), polyvinyl chloride, polystyrene, polyamides, nylon, polycarbonates, polysulfides, polysulfones, hydrogels (e.g., acrylics), polyacrylonitrile, polyvinylacetate, cellulose acetate butyrate, nitrocellulose, copolymers of urethane/carbonate, copolymers of styrene/maleic acid, poly(ethylenimine), hyaluron, heparin, agarose, pullulan, and copolymers, terpolymers, and copolymers comprising any combinations thereof.

In some embodiments, the polymer is a biocompatible polymer. As used herein, the term "biocompatible" means exhibition of essentially no cytotoxicity or immunogenicity while in contact with body fluids or tissues. The term "biocompatible polymer" refers to polymers which are non-toxic, chemically inert, and substantially non-immunogenic when used internally in a subject and which are substantially insoluble in blood. The biocompatible polymer can be either non-biodegradable or preferably biodegradable. Preferably, the biocompatible polymer is also non-inflammatory when employed in situ.

Biodegradable polymers are disclosed in the art. Examples of suitable biodegradable polymers include, but are not limited to, linear-chain polymers such as polypeptides, polynucleotides, polysaccharides, polylactides, polyglycolides, polycaprolactones, copolymers of polylactic acid and polyglycolic acid, polyanhydrides, polyepsilon caprolactone, polyamides, polyurethanes, polyesteramides, polyorthoesters, polydioxanones, polyacetals, polyketals, polycarbonates, polyorthocarbonates, polydihydropyrans, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, polymethyl methacrylate, chitin, chitosan, copolymers of polylactic acid and polyglycolic acid, poly(glycerol sebacate) (PGS), fumaric acid, sebacic acid, and copolymers, terpolymers including one or more of the foregoing. Other biodegradable polymers include, for example, gelatin, collagen, silk, chitosan, alginate, cellulose, poly-nucleic acids, etc.

Suitable non-biodegradable biocompatible polymers include, by way of example, cellulose acetates (including cellulose diacetate), polyethylene, polypropylene, polybutylene, polyethylene terphthalate (PET), polyvinyl chloride, polystyrene, polyamides, nylon, polycarbonates, polysulfides, polysulfones, hydrogels (e.g., acrylics), polyacrylonitrile, polyvinylacetate, cellulose acetate butyrate, nitrocellulose, copolymers of urethane/carbonate, copolymers of styrene/maleic acid, poly(ethylenimine), Poloxamers (e.g., Pluronic such as Poloxamers 407 and 188), hyaluronic acid, heparin, agarose, Pullulan, and copolymers including one or more of the foregoing, such as ethylene/vinyl alcohol copolymers (EVOH).

In some embodiments, the biocompatible polymer is a copolymer of polylactic acid and polyglycolic acid, poly (glycerol sebacate) (PGS), poly(ethylenimine), Pluronic (Poloxamers 407, 188), hyaluronic acid, heparin, agarose, or Pullulan.

In some embodiments, the polymer is a homopolymer, a copolymer or a block polymer.

In some embodiments, the polymer comprises side chains selected from the group consisting of amide or ester groups. In some embodiments, the polymer is biodegradable, biocompatible, and non-toxic.

The polymer can be derivatized with a second polymer and the first polymer and the second polymer can be the same or different. For example, the polymer can be derivatized with a polyethylene glycol (PEG).

In some embodiments, polymers or portions of polymers can be connected by linkers. In some embodiments, components of a polymeric particle, e.g., a payload molecule or monocyte-targeting and/or macrophage-targeting ligand can be connected via a linker. As used herein, the term "linker" refers to a moiety that connects two parts of a compound. Linkers typically comprise a direct bond or an atom such as oxygen or sulfur, a unit such as $NR_1$, $C(O)$, $C(O)O$, $C(O)NR_1$, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkynylheteroarylalkyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R_1)_2$, C(O), cleavable linking group, substituted or unsubstituted aryl, substituted or unsubstituted heteroaryl, substituted or unsubstituted heterocyclic; where $R_1$ is hydrogen, acyl, aliphatic or substituted aliphatic.

The linker can be a branched linker. The branch-point of the branched linker can be at least divalent, but can be a trivalent, tetravalent, pentavalent or hexavalent atom, or a group presenting such multiple valencies. In certain embodiments, the branch-point can be, —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments, the branch-point can be an acrylate, cyanoacrylate, or methylacrylate.

In various embodiments, the linker is a cleavable linker. A cleavable linker means that the linker can be cleaved to release the two parts the linker is holding together. A cleavable linker can be susceptible to cleavage agents, such as, but not limited to, enzymes, pH, redox potential or the presence of degradative molecules. Examples of such agents: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

In some embodiments, the linker is polyethylene glycol. In some embodiments, the linker is a peptide comprising the sequence DEVD (SEQ ID NO: 1). In a further embodiment, the linker is a peptide comprising the sequence KDEVDAP (SEQ ID NO: 2). In still a further embodiment, the linker is a peptide comprising the sequence GKDEVDAP (SEQ ID NO: 3). In some embodiments, the cleavable linker is cleavable by an enzyme.

In some embodiments, the cleavable linker is selected from a group consisting of small molecules. In some preferred embodiments, the cleavable linker is selected from a group consisting of peptides or polypeptides.

In one aspect of any of the embodiments, described herein is a method of producing a polymeric particle as described herein the method comprising:
  a. applying a layer-by-layer coating of one or more cell adhesive molecules to a stamp, e.g., with micropatterned features made by soft lithography to form the first region;
  b. applying the one or more structural polymers to the stamp with a spin coater to form the second region;
  c. printing the resulting two regions onto a surface coated with poly(vinyl alcohol) (PVA) and peeling away the stamp; and
  d. contacting the product of step c with an aqueous solution to release the polymeric particles.

In one aspect of any of the embodiments, described herein is a method of producing a polymeric particle as described herein, the method comprising:

a. applying a layer-by-layer coating of one or more cell adhesive molecules (e.g., polyelectrolytes) to a stamp with micropatterned features made by soft lithography to form the first region;
b. applying the one or more structural polymers to the stamp with a spin coater to form a first layer of the second region;
c. applying the payload molecule and/or PVA to form the third region;
d. applying the one or more structural polymers to the stamp with a spin coater to form a second layer of the second region;
e. printing the product resulting from step d onto a surface coated with poly(vinyl alcohol) (PVA) and peeling away the stamp; and contacting the product of step e with an aqueous solution to release the polymeric particles. These methods can comprise the use of layer-by-layer techniques, which, along with general procedures for suitable methods of fabrication, are described in further detail in US Patent Publication 2004/01152791; Park et al. *Advanced Materials* 2005 17:2575-2579; and Decher et al. "Multilayer Thin Films: Sequential Assembly of Nanocomposite Materials" 2012 John Wiley & Sons; each of which is incorporated by reference herein in its entirety.

In some embodiments of any of the aspects, the stamp comprises circular columns. In some embodiments of any of the aspects, the stamp is a polydimethylsiloxane (PDMS) stamp. In some embodiments of any of the aspects, the one or more structural polymers are applied as a solution, e.g., a solution in acetone. In some embodiments of any of the aspects, the PVA on the surface has been previously exposed to water vapor.

In one aspect of any of the embodiments, described herein is a method of treating cancer and/or a tumor in a subject in need thereof, the method comprising administering to the subject an engineered cellular composition as described herein, wherein the polarizing agent is an M1-polarizing agent. In some embodiments of any of the aspects, the method further comprises administering radiation or at least one chemotherapy to the subject.

In one aspect of any of the embodiments, described herein is a method of treating a fracture, wound, or infection in a subject in need thereof, the method comprising administering to the subject an engineered cellular composition as described herein, wherein the polarizing agent is an M2-polarizing agent.

In one aspect of any of the embodiments, described herein is a method of treating inflammation in a subject in need thereof, the method comprising administering to the subject an engineered cellular composition as described herein, wherein the polarizing agent is an M2-polarizing agent. In some embodiments of any of the aspects, the inflammation is in the lungs and is caused by or arises from infection or injury. In some embodiments of any of the aspects, the inflammation is in the joints and is caused by or arises from arthritis. In some embodiments of any of the aspects, the inflammation is in the skin and is caused by or arises from infection or autoimmune disorder. In some embodiments of any of the aspects, the inflammation is caused by, arises from, or is a symptom of acute respiratory distress (ARDS), arthritis, infection, or an autoimmune disorder. In some embodiments of any of the aspects of treating inflammation, the polarizing agent is cytokine, e.g., an IL-4 polypeptide.

The engineered cellular compositions can comprise cells, which are autologous to or heterologous to the subject to be treated. In some embodiments of any of the aspects, the method of treatment can comprise a first step of obtaining the cell from a donor and/or the subject and contacting the cell with the polymeric particle ex vivo. The cell can be isolated, e.g., isolated from a blood sample obtained from the donor/subject prior to performing the contacting/adhering step, or the contacting/adhering can take place in a sample comprising multiple cell types, e.g., in a blood sample.

The methods described herein can further comprise steps of localizing the engineered cellular composition to a desired location or disrupting/degrading/releasing the polymeric particle at a desired time or location. Described above herein are polymeric particles that are responsive to such controlled and/or inducible stimuli. In some embodiments of any of the aspects, the second region of the polymeric particle comprises poly(lactic-co-caprolactone) (PLCL) and the method further comprises increasing the temperature of at least one area of the subject in order to permit the cell to phagocytose the polymeric particles. In some embodiments of any of the aspects, the second region of the polymeric particle comprises a near-infrared degradable polymer or polymer linker and the method further comprises subject at least one area of the subject to near-infrared light in order to permit the cell to phagocytose the polymeric particles. In some embodiments of any of the aspects, the polymeric particle comprises an echogenic liposome and the method further comprises subject at least one area of the subject to ultrasound in order to permit the cell to phagocytose the polymeric particles or to release a payload molecule. In some embodiments of any of the aspects, the polymeric particle comprises a magnetic nanoparticle and the method further comprises subject at least one area of the subject to a magnetic field in order to permit the cell to phagocytose the polymeric particles or to release a payload molecule. In some embodiments of any of the aspects, the polymeric particle comprises a gold nanoparticle and the method further comprises subject at least one area of the subject to an electromagnetic wave in order to permit the cell to phagocytose the polymeric particles or to release a payload molecule.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor. As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

As used herein the term "neoplasm" refers to any new and abnormal growth of tissue, e.g., an abnormal mass of tissue, the growth of which exceeds and is uncoordinated with that of the normal tissues. Thus, a neoplasm can be a benign neoplasm, premalignant neoplasm, or a malignant neoplasm.

A subject that has a cancer or a tumor is a subject having objectively measurable cancer cells present in the subject's body. Included in this definition are malignant, actively proliferative cancers, as well as potentially dormant tumors or micrometastatses. Cancers that migrate from their original location and seed other vital organs can eventually lead to the death of the subject through the functional deterioration of the affected organs.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm.; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulvar cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs syndrome.

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

As used herein, "inflammation" refers to the complex biological response to harmful stimuli, such as pathogens, damaged cells, or irritants. Inflammation is a protective attempt by the organism to remove the injurious stimuli as well as initiate the healing process for the tissue. Accordingly, the term "inflammation" includes any cellular process that leads to the production of pro-inflammatory cytokines, inflammation mediators and/or the related downstream cellular events resulting from the actions of the cytokines thus produced, for example, fever, fluid accumulation, swelling, abscess formation, and cell death. Inflammation can include both acute responses (i.e., responses in which the inflammatory processes are active) and chronic responses (i.e., responses marked by slow progression and formation of new connective tissue). Acute and chronic inflammation may be distinguished by the cell types involved. Acute inflammation often involves polymorphonuclear neutrophils; whereas chronic inflammation is normally characterized by a lymphohistiocytic and/or granulomatous response.

An inflammatory condition is any disease state characterized by inflammatory tissues (for example, infiltrates of leukocytes such as lymphocytes, neutrophils, macrophages, eosinophils, mast cells, basophils and dendritic cells) or inflammatory processes which provoke or contribute to the abnormal clinical and histological characteristics of the disease state. Inflammatory conditions include, but are not limited to, inflammatory conditions of the skin, inflammatory conditions of the lung, inflammatory conditions of the joints, inflammatory conditions of the gut, inflammatory conditions of the eye, inflammatory conditions of the endocrine system, inflammatory conditions of the cardiovascular system, inflammatory conditions of the kidneys, inflammatory conditions of the liver, inflammatory conditions of the central nervous system, or sepsis-associated conditions. In some embodiments, the inflammatory condition is associated with wound healing. In some embodiments, the inflammation to be treated according to the methods described herein can be skin inflammation; inflammation caused by substance abuse or drug addiction; inflammation associated with infection; inflammation of the cornea; inflammation of the retina; inflammation of the spinal cord; inflammation associated with organ regeneration; and pulmonary inflammation.

In some embodiments, an inflammatory condition can be an autoimmune disease. Non-limiting examples of autoimmune diseases can include: Type 1 diabetes; systemic lupus erythematosus; rheumatoid arthritis; psoriasis; inflammatory bowel disease; Crohn's disease; and autoimmune thyroiditis.

In some embodiments, a subject in need of treatment for inflammation can be a subject having, or diagnosed as having temporomandibular joint disorders; COPD; smoke-induced lung injury; renal dialysis associated disorders; spinal cord injury; graft vs. host disease; bone marrow transplant or complications thereof; infection; trauma; pain; incisions; surgical incisions; a chronic pain disorder; a chronic bone disorder; mastitis; and joint disease. In some embodiments, trauma can include battle-related injuries or tissue damage occurring during a surgery. Smoke-induced lung injury can result from exposure to tobacco smoke, environmental pollutants (e.g. smog or forest fires), or industrial exposure. By way of non-limiting example, inflammatory conditions can be inflammatory conditions of the skin, such as Sweet's syndrome, pyoderma gangrenosum, subcorneal pustular dermatosis, erythema elevatum diutinum, Behcet's disease or acute generalized exanthematous pustulosis, a bullous disorder, psoriasis, a condition resulting in pustular lesions, acne, acne vulgaris, dermatitis (e.g. contact dermatitis, atopic dermatitis, seborrheic dermatitis, eczematous dermatitides, eczema craquelee, photoallergic dermatitis, phototoxicdermatitis, phytophotodermatitis, radiation dermatitis, stasis dermatitis or allergic contact dermatitis), eczema, ulcers and erosions resulting from trauma, burns, ischemia of the skin or mucous membranes, several forms of ichthyoses, epidermolysis bullosae, hypertrophic scars, keloids, cutaneous changes of intrinsic aging, photoaging, frictional blistering caused by mechanical shearing of the skin, cutaneous atrophy resulting from the topical use of corticosteroids, and inflammation of mucous membranes (e.g., cheilitis, chapped lips, nasal irritation, mucositis and vulvovaginitis).

By way of non-limiting example, inflammatory conditions can be inflammatory conditions of the lung, such as asthma, bronchitis, chronic bronchitis, bronchiolitis, pneumonia, sinusitis, emphysema, adult respiratory distress syndrome, pulmonary inflammation, pulmonary fibrosis, and cystic fibrosis (which may additionally or alternatively involve the gastro-intestinal tract or other tissue(s)). By way of non-limiting example, inflammatory conditions can be inflammatory conditions of the joints, such as rheumatoid arthritis, rheumatoid spondylitis, juvenile rheumatoid arthritis, osteoarthritis, gouty arthritis, infectious arthritis, psoriatic arthritis, and other arthritic conditions. By way of non-limiting example, inflammatory conditions can be inflammatory conditions of the gut or bowel, such as inflammatory bowel disease, Crohn's disease, ulcerative colitis and distal proctitis. By way of non-limiting example, inflammatory conditions can be inflammatory conditions of the eye, such as dry eye syndrome, uveitis (including iritis), conjunctivitis, scleritis, and keratoconjunctivitis sicca. By way of non-limiting example, inflammatory conditions can be inflammatory conditions of the endocrine system, such as autoimmune thyroiditis (Hashimoto's disease), Graves' disease, Type I diabetes, and acute and chronic inflammation of the adrenal cortex. By way of non-limiting example, inflammatory conditions can be inflammatory conditions of the cardiovascular system, such as coronary infarct damage, peripheral vascular disease, myocarditis, vasculitis, revascularization of stenosis, artherosclerosis, and vascular disease associated with Type II diabetes. By way of non-limiting example, inflammatory conditions can be inflammatory conditions of the kidneys, such as glomerulonephritis, interstitial nephritis, lupus nephritis, and nephritis secondary to Wegener's disease, acute renal failure secondary to acute nephritis, post-obstructive syndrome and tubular ischemia. By way of non-limiting example, inflammatory conditions can be inflammatory conditions of the liver, such as hepatitis (arising from viral infection, autoimmune responses, drug treatments, toxins, environmental agents, or as a secondary consequence of a primary disorder), biliary atresia, primary biliary cirrhosis and primary sclerosing cholangitis. By way of non-limiting example, inflammatory conditions can be inflammatory conditions of the central nervous system, such as multiple sclerosis and neurodegenerative diseases such as Alzheimer's disease or dementia associated with HIV infection. By way of non-limiting example, inflammatory conditions can be inflammatory conditions of the central nervous system, such as MS; all types of encephalitis and meningitis; acute disseminated encephalomyelitis; acute transverse myelitis; neuromyelitis optica; focal demyelinating syndromes (e.g., Balo's concentric sclerosis and Marburg variant of MS); progressive multifocal leukoencephalopathy; subacute sclerosing panencephalitis; acute haemorrhagic leucoencephalitis (Hurst's disease); human T-lymphotropic virus type-1associated myelopathy/tropical spactic paraparesis; Devic's disease; human immunodeficiency virus encephalopathy; human immunodeficiency virus vacuolar myelopathy; peripheral neuropathies; Guillain-Barre Syndrome and other immune mediated neuropathies; and myasthenia gravis. By way of non-limiting example, inflammatory conditions can be sepsis-associated conditions, such as systemic inflammatory response syndrome (SIRS), septic shock or multiple organ dysfunction syndrome (MODS). Further non-limiting examples of inflammatory conditions include, endotoxin shock, periodontal disease, polychondritis; periarticular disorders; pancreatitis; system lupus erythematosus; Sjogren's syndrome; vasculitis sarcoidosis amyloidosis; allergies; anaphylaxis; systemic mastocytosis; pelvic inflammatory disease; multiple sclerosis; multiple sclerosis (MS); celiac disease, Guillain-Barre syndrome, sclerosing cholangitis, autoimmune hepatitis, Raynaud's phenomenon, Goodpasture's syndrome, Wegener's granulomatosis, polymyalgia rheumatica, temporal arteritis/giant cell arteritis, chronic fatigue syndrome CFS), autoimmune Addison's Disease, ankylosing spondylitis, Acute disseminated encephalomyelitis, antiphospholipid antibody syndrome, aplastic anemia, idiopathic thrombocytopenic purpura, Myasthenia gravis, opsoclonus myoclonus syndrome, optic neuritis, Ord's thyroiditis, pemphigus, pernicious anaemia, polyarthritis in dogs, Reiter's syndrome, Takayasu's arteritis, warm autoimmune hemolytic anemia, fibromyalgia (FM), autoinflammatory PAPA syndrome, Familial Mediaterranean Fever, polymyalgia rheumatica, polyarteritis nodosa, churg strauss syndrome; fibrosing alveolitis, hypersensitivity pneumonitis, allergic aspergillosis, cryptogenic pulmonary eosinophilia, bronchiolitis obliterans organising pneumonia; urticaria; lupoid hepatitis; familial cold autoinflammatory syndrome, Muckle-Wells syndrome, the neonatal onset multisystem inflammatory disease, graft rejection (including allograft rejection and graft-v-host disease), otitis, chronic obstructive pulmonary disease, sinusitis, chronic prostatitis, reperfusion injury, silicosis, inflammatory myopathies, hypersensitivities and migraines. In some embodiments, an inflammatory condition is associated with an infection, e.g., viral, bacterial, fungal, parasite or prion infections. In some embodiments, an inflammatory condition is associated with an allergic response. In some embodiments, an inflammatory condition is associated with a pollutant (e.g., asbestosis, silicosis, or berylliosis).

In some embodiments, the inflammatory condition can be a local condition, e.g., a rash or allergic reaction. In some embodiments, the inflammation is associated with a wound.

In some embodiments, the technology described herein relates to methods of promoting wound healing. As used herein, "wound" refers broadly to injuries to an organ or tissue of an organism that typically involves division of tissue or rupture of a membrane (e.g., skin), due to external violence, a mechanical agency, or infectious disease. A wound can be an epithelial, endothelial, connective tissue, ocular, or any other kind of wound in which the strength and/or integrity of a tissue has been reduced, e.g. trauma has caused damage to the tissue. The term "wound" encompasses injuries including, but not limited to, lacerations, abrasions, avulsions, cuts, burns, velocity wounds (e.g., gunshot wounds), penetration wounds, puncture wounds, contusions, diabetic wounds, hematomas, tearing wounds, and/or crushing injuries. In one aspect, the term "wound" refers to an injury to the skin and subcutaneous tissue initiated in any one of a variety of ways (e.g., pressure sores from extended bed rest, wounds induced by trauma, cuts, ulcers, burns and the like) and with varying characteristics. As used herein, the term "wound healing" refers to a process by which the body of a wounded organism initiates repair of a tissue at the wound site (e.g., skin). The wounds healing process requires, in part, angiogenesis and revascularization of the wounded tissue. Wound healing can be measured by assessing such parameters as contraction, area of the wound, percent closure, percent closure rate, and/or infiltration of blood vessels as known to those of skill in the art. In some embodiments, the particles and compositions described herein can be applied topically to promote wound healing.

The compositions and methods described herein can be administered to a subject having or diagnosed as having one of the conditions described herein. In some embodiments, the methods described herein comprise administering an effective amount of compositions described herein, e.g. an engineered cellular composition to a subject in order to alleviate a symptom of a condition described herein. In some embodiments of any of the aspects, a therapeutically effective dose of the composition is administered. As used herein, "alleviating a symptom" is ameliorating any condition or symptom associated with the disease. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to parenteral, intravenous, intramuscular, subcutaneous, transdermal, airway (aerosol), pulmonary, cutaneous, injection, or intratumoral administration. Administration can be local or systemic.

The term "effective amount" as used herein refers to the amount of a composition needed to alleviate at least one or more symptom of the disease or disorder, and relates to a sufficient amount of pharmacological composition to provide the desired effect. The term "therapeutically effective amount" therefore refers to an amount of a composition that is sufficient to provide a particular therapeutic effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the active ingredient which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g. for tumor size and/or inflammatory markers, among others. The dosage can be determined by a physician and adjusted, as necessary, to suit observed effects of the treatment.

In some embodiments of any of the aspects, a composition described herein can be a pharmaceutical composition. In some embodiments, the technology described herein relates to a pharmaceutical composition comprising an engineered cellular composition as described herein, and optionally a pharmaceutically acceptable carrier. In some embodiments, the active ingredients of the pharmaceutical composition comprise an engineered cellular composition as described herein. In some embodiments, the active ingredients of the pharmaceutical composition consist essentially of an engineered cellular composition as described herein. In some embodiments, the active ingredients of the pharmaceutical composition consist of an engineered cellular composition as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, as described herein.

In some embodiments, the pharmaceutical composition comprising an engineered cellular composition as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry or lyophilized products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS°-type dosage forms and dose-dumping.

Suitable vehicles that can be used to provide parenteral dosage forms of an engineered cellular composition as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

In some embodiments of any of the aspects, the engineered cellular composition described herein is administered as a monotherapy, e.g., another treatment for the condition is not administered to the subject.

In some embodiments of any of the aspects, the methods described herein can further comprise administering a second agent and/or treatment to the subject, e.g. as part of a combinatorial therapy. Non-limiting examples of a second agent and/or treatment can include radiation therapy, surgery, gemcitabine, cisplastin, paclitaxel, carboplatin, bortezomib, AMG479, FK506, vorinostat, acriflavine, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., *Agnew. Chem. Intl. Ed. Engl.*, 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

In addition, the methods of treatment can further include the use of radiation or radiation therapy. Further, the methods of treatment can further include the use of surgical treatments.

By way of non-limiting example, if a subject is to be treated for inflammation according to the methods described herein, the subject can also be administered a second agent and/or treatment known to be beneficial for subjects suffering from pain or inflammation. Examples of such agents and/or treatments include, but are not limited to, non-steroidal anti-inflammatory drugs (NSAIDs—such as aspirin, ibuprofen, or naproxen); corticosteroids, including glucocorticoids (e.g. cortisol, prednisone, prednisolone, methylprednisolone, dexamethasone, betamethasone, triamcinolone, and beclometasone); methotrexate; sulfasalazine; leflunomide; anti-TNF medications; cyclophosphamide; pro-resolving drugs; mycophenolate; or opiates (e.g., endorphins, enkephalins and dynorphin), steroids, analgesics, barbiturates, oxycodone, morphine, lidocaine and the like.

In certain embodiments, an effective dose of a composition comprising an engineered cellular composition as described herein can be administered to a patient once. In certain embodiments, an effective dose of a composition can be administered to a patient repeatedly. In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the composition. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an engineered cellular composition as described herein can be administered over a period of time, such as over a 5 minute, 10 minute, 15 minute, 20 minute, or 25 minute period.

The dosage ranges for the administration of the compositions described herein, according to the methods described herein depend upon, for example, the potency of the cells, and the extent to which symptoms, markers, or indicators of a condition described herein are desired to be reduced, for example the percentage reduction desired for tumor growth or the extent to which, for example, wound healing are desired to be induced. The dosage should not be so large as to cause adverse side effects, such as excessive inflammation or immunosuppression. Generally, the dosage will vary with the age, condition, and sex of the patient and can be determined by one of skill in the art. The dosage can also be adjusted by the individual physician in the event of any complication.

The efficacy of an engineered cellular composition in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g., pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response. It is well within the ability of one skilled in the art to monitor efficacy of administration and/or treatment by measuring any one of such parameters, or any combination of parameters. Efficacy can be assessed in animal models of a condition described herein, for example treatment of cancer. When using an experimental animal model, efficacy of treatment is evidenced when a statistically significant change in a marker is observed, e.g., tumor growth, tumor size, inflammation, wound size, etc.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of a disease. A subject can be male or female.

A subject can be one who has been previously diagnosed with or identified as suffering from or having a condition in need of treatment or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

The terms "compound" and "agent" refer to any entity which is normally not present or not present at the levels being administered and/or provided to a cell, tissue or subject. An agent can be selected from a group comprising: chemicals; small organic or inorganic molecules; signaling molecules; nucleic acid sequences; nucleic acid analogues; proteins; peptides; enzymes; aptamers; peptidomimetic, peptide derivative, peptide analogs, antibodies; intrabodies; biological macromolecules, extracts made from biological materials such as bacteria, plants, fungi, or animal cells or tissues; naturally occurring or synthetic compositions or functional fragments thereof. In some embodiments, the agent is any chemical, entity or moiety, including without limitation synthetic and naturally occurring non-proteinaceous entities. In certain embodiments the agent is a small molecule having a chemical moiety. For example, chemical moieties include unsubstituted or substituted alkyl, aromatic, or heterocyclyl moieties including macrolides, leptomycins and related natural products or analogues thereof. Agents can be known to have a desired activity and/or property or can be selected from a library of diverse compounds.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

As used herein, the terms "protein" and "polypeptide" are used interchangeably herein to designate a series of amino acid residues, connected to each other by peptide bonds between the alpha-amino and carboxyl groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. the M1-polarizing activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments, the polypeptide described herein (or a nucleic acid encoding such a polypeptide) can be a functional fragment of one of the amino acid sequences described herein. As used herein, a "functional fragment" is a fragment or segment of a peptide, which retains at least 50% of the wild type reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (*Gene* 42:133, 1986); Bauer et al. (*Gene* 37:73, 1985); Craik (*BioTechniques*, January 1985, 12-19); Smith et al. (Genetic Engineering: Principles and Methods, Plenum. Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a condition. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in in nature.

As used herein, the term "administering," refers to the placement of a compound as disclosed herein into a subject by a method or route, which results in at least partial delivery of the agent at a desired site. Pharmaceutical compositions comprising the compounds disclosed herein can be administered by any appropriate route, which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

In some events, such as with Hyaluronic acid with aldehyde modifications, the specific binding can be accompanied by covalent binding to strengthen the cell/particle interaction.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example".

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

One of skill in the art can readily identify a chemotherapeutic agent of use (e.g. see Physicians' Cancer Chemotherapy Drug Manual 2014, Edward Chu, Vincent T. DeVita Jr., Jones & Bartlett Learning; Principles of Cancer Therapy, Chapter 85 in Harrison's Principles of Internal Medicine, 18th edition; Therapeutic Targeting of Cancer Cells: Era of Molecularly Targeted Agents and Cancer Pharmacology, Chs. 28-29 in Abeloff's Clinical Oncology, 2013 Elsevier; and Fischer D S (ed): The Cancer Chemotherapy Handbook, 4th ed. St. Louis, Mosby-Year Book, 2003).

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. An engineered cellular composition comprising:
   a. a monocyte or macrophage cell; and
   b. a polymeric particle comprising an M1-polarizing cytokine polypeptide, wherein the particle is located on the cell surface of the monocyte or macrophage.
2. The composition of paragraph 1, wherein the polymeric particle is substantially discoidal in shape.
3. The composition of paragraph 1, wherein the polymeric particle is discoidal in shape.
4. The composition of any of paragraphs 1-3, wherein the polymeric particle is about 3 µm×150 nm in size to about 12 µm×500 nm in size.
5. The composition of any of paragraphs 1-4, wherein the polymeric particle is about 6 µm×250 nm in size.
6. The composition of any of paragraphs 1-5, wherein the polymeric particle comprises:
   a. a first region comprising one or more cell adhesive molecules (e.g., polyelectrolytes);
   b. a second region comprising one or more structural polymers.
7. The composition of paragraph 6, wherein the cell adhesive polyelectrolytes comprise hyaluronic acid and/or poly(allylamine) hydrochloride.
8. The composition of paragraph 7, wherein the hyaluronic acid is modified to comprise aldehyde groups.
9. The composition of any of paragraphs 6-8, wherein the structural polymer comprises poly(lactic-co-glycolic) acid (PLGA) or Poly(glycerol sebacate) (PGS).
10. The composition of any of paragraphs 6-9, wherein the structural polymer is a 10 wt % solution of the structural polymer.
11. The composition of any of paragraphs 6-10, wherein the second region further comprises Poly(lactic-co-capalactone) (PLCL).
12. The composition of any of paragraphs 6-11, wherein the second region comprises or further comprises a near-infrared degradable polymer or polymer linker.
13. The composition of any of paragraphs 1-12, wherein the polymeric particle further comprises one or more monocyte-targeting and/or macrophage-targeting ligands.
14. The composition of paragraph 13, wherein the monocyte-targeting and/or macrophage-targeting ligand is located in the region comprising cell adhesive molecules (e.g., polyelectrolytes).
15. The composition of any of paragraphs 13-14, wherein the monocyte-targeting and/or macrophage-targeting ligand is IgG, an antibody, a polypeptide, or an aptamer.
16. The composition of any of paragraphs 1-15, wherein the polymeric particle further comprises one or more payload molecules.
17. The composition of paragraph 16, wherein the payload molecule is a small molecule or polypeptide.
18. The composition of any of paragraphs 16-17, wherein the payload molecule is present in admixture with the structural polymer.
19. The composition of any of paragraphs 16-18, wherein the payload molecule is present in a third region of the polymeric particle which is located between the first and second regions.
20. The composition of any of paragraphs 1-19, wherein the polymeric particle further comprises an echogenic liposome.
21. The composition of any of paragraphs 1-20, wherein the polymeric particle further comprises a magnetic nanoparticle.
22. The composition of any of paragraphs 1-21, wherein the polymeric particle further comprises a gold nanoparticle.
23. The composition of any of paragraphs 1-22, wherein a region is a layer.
24. The composition of any of paragraphs 1-23, wherein the cell is a monocyte.

25. The composition of any of paragraphs 1-23, wherein the cell is a macrophage.
26. The composition of paragraph 25, wherein the macrophage is an M1 macrophage.
27. The composition of any of paragraphs 1-26, wherein the M1 polarizing cytokine is IFN-γ or IL-4.
28. A method of treating cancer and/or a tumor in a subject in need thereof, the method comprising administering to the subject the engineered cellular composition of any of paragraphs 1-27.
29. The method of paragraph 28, further comprising administering radiation or at least one chemotherapy to the subject.
30. A method of treating a fracture, wound, or infection in a subject in need thereof, the method comprising administering to the subject the engineered cellular composition of any of paragraphs 1-27.
31. A method of treating inflammation in a subject in need thereof, the method comprising administering to the subject the engineered cellular composition of any of paragraphs 1-27.
32. The method of paragraph 31, wherein the inflammation is acute respiratory distress syndrome (ARDS).
33. The method of any of paragraphs 31-32, wherein the polymeric particle comprises IL-4.
34. The method of any of paragraphs 28-33, wherein the cell is autologous to the subject.
35. The method of any of paragraphs 28-33, wherein the cell is heterologous to the subject.
36. The method of any of paragraphs 28-35, further comprising a first step of obtaining the cell from a donor and/or the subject and contacting the cell with the polymeric particle ex vivo.
37. The method of any of paragraphs 28-36, wherein a therapeutically effective dose of the composition is administered.
38. The method of any of paragraphs 28-37, wherein the second region of the polymeric particle comprises Poly(lactic-co-capalactone) (PLCL) and the method further comprises increasing the temperature of at least one area of the subject in order to permit the cell to phagocytose the polymeric particles.
39. The method of any of paragraphs 28-38, wherein the second region of the polymeric particle comprises a near-infrared degradable polymer or polymer linker and the method further comprises subject at least one area of the subject to near-infrared light in order to permit the cell to phagocytose the polymeric particles.
40. The method of any of paragraphs 28-39, wherein the polymeric particle comprises an echogenic liposome and the method further comprises subject at least one area of the subject to ultrasound in order to permit the cell to phagocytose the polymeric particles or to release a payload molecule.
41. The method of any of paragraphs 28-40, wherein the polymeric particle comprises an magnetic nanoparticle and the method further comprises subject at least one area of the subject to a magnetic field in order to permit the cell to phagocytose the polymeric particles or to release a payload molecule.
42. The method of any of paragraphs 28-41, wherein the polymeric particle comprises a gold nanoparticle and the method further comprises subject at least one area of the subject to an electromagnetic wave in order to permit the cell to phagocytose the polymeric particles or to release a payload molecule.

43. A method of producing a polymeric particle of any of paragraphs 6-27, the method comprising:
   a. applying a layer by layer coating of one or more cell adhesive molecules (e.g., polyelectrolytes) to a stamp to form the first region;
   b. applying the one or more structural polymers to the stamp with a spin coater to form the second region;
   c. printing the resulting two regions onto a surface coated with Poly(vinyl alcohol) (PVA) and peeling away the stamp; and
   d. contacting the product of step c with an aqueous solution to release the polymeric particles.
44. The method of paragraph 43, wherein the stamp comprises circular columns.
45. The method of any of paragraphs 43-44, wherein the stamp is a PDMS stamp.
46. The method of any of paragraphs 43-45, wherein the one or more structural polymers are applied as a solution.
47. The method of any of paragraphs 43-46, wherein the one or more structural polymers are applied as a solution in acetone.
48. The method of any of paragraphs 43-47, wherein the PVA on the surface has been exposed to water vapor prior to step c.
49. A polymeric particle comprising an M1 polarizing cytokine polypeptide.
50. The particle of paragraph 49, wherein the polymeric particle is substantially discoidal in shape.
51. The particle of paragraph 49, wherein the polymeric particle is discoidal in shape.
52. The particle of any of paragraphs 49-51, wherein the polymeric particle is about 3 μm×150 nm in size to about 12 μm×500 nm in size.
53. The particle of any of paragraphs 49-52, wherein the polymeric particle is about 6 μm×250 nm in size.
54. The particle of any of paragraphs 49-53, wherein the polymeric particle comprises:
   a. a first region comprising one or more cell adhesive molecules (e.g., polyelectrolytes);
   b. a second region comprising one or more structural polymers.
55. The particle of paragraph 54, wherein the cell adhesive polyelectrolytes comprise hyaluronic acid and/or poly(allylamine) hydrochloride.
56. The particle of paragraph 55, wherein the hyaluronic acid is modified to comprise aldehyde groups.
57. The particle of any of paragraphs 54-56, wherein the structural polymer comprises poly(lactic-co-glycolic) acid (PLGA) or Poly(glycerol sebacate) (PGS).
58. The particle of any of paragraphs 54-57, wherein the structural polymer is a 10 wt % solution of the structural polymer.
59. The particle of any of paragraphs 54-58, wherein the second region further comprises Poly(lactic-co-capalactone) (PLCL).
60. The particle of any of paragraphs 54-59, wherein the second region comprises or further comprises a near-infrared degradable polymer or polymer linker.
61. The particle of any of paragraphs 49-60, wherein the polymeric particle further comprises one or more monocyte-targeting and/or macrophage-targeting ligands.
62. The particle of paragraph 61, wherein the monocyte-targeting and/or macrophage-targeting ligand is located in the region comprising cell adhesive polyelectrolytes.

63. The particle of any of paragraphs 61-62, wherein the monocyte-targeting and/or macrophage-targeting ligand is IgG, an antibody, a polypeptide, or an aptamer.
64. The particle of any of paragraphs 49-63, wherein the polymeric particle further comprises one or more payload molecules.
65. The particle of paragraph 64, wherein the payload molecule is a small molecule or polypeptide.
66. The particle of any of paragraphs 64-65, wherein the payload molecule is present in admixture with the structural polymer.
67. The particle of any of paragraphs 64-66, wherein the payload molecule is present in a third region of the polymeric particle which is located between the first and second regions.
68. The particle of any of paragraphs 49-67, wherein the polymeric particle further comprises an echogenic liposome.
69. The particle of any of paragraphs 49-68, wherein the polymeric particle further comprises a magnetic nanoparticle.
70. The particle of any of paragraphs 49-69, wherein the polymeric particle further comprises a gold nanoparticle.
71. The particle of any of paragraphs 49-70, wherein a region is a layer.
72. The particle of any of paragraphs 49-71, wherein the M1 polarizing cytokine is IFN-γ or IL-4.

Some embodiments of the technology described herein can be defined according to any of the following numbered paragraphs:

1. An engineered cellular composition comprising:
   a. a monocyte or macrophage cell; and
   b. a polymeric particle comprising at least one polarizing agent, wherein the particle is located on the cell surface of the monocyte or macrophage.
2. The composition of paragraph 1, wherein the cell is a monocyte.
3. The composition of paragraph 1, wherein the cell is a macrophage.
4. The compostion of paragraph 3, wherein the macrophage is an M0 macrophage.
5. The composition of paragraph 3, wherein the macrophage is an M1-polarized macrophage.
6. The composition of paragraph 3, wherein the macrophage is an M2-polarized macrophage.
7. The composition of paragraph 1, whereby the macrophage is substantially driven to an M1 or M2 phenotype.
8. The composition of any of paragraphs 1-7, wherein the polarizing agent is an M1-polarizing agent.
9. The composition of any of paragraphs 1-7, wherein the polarizing agent is an M2-polarizing agent.
10. The composition of any of paragraphs 1-9, wherein the particle further comprises a therapeutic agent.
11. An engineered cellular composition comprising:
    a. a monocyte or macrophage cell; and
    b. a polymeric particle comprising at least one M1-polarizing agent or at least one M2-polarizing agent, wherein the particle is located on the cell surface of the monocyte or macrophage.
12. The composition of paragraph 8 or 11, wherein the M1-polarizing agent is selected from the group consisting of:
    IFN-γ; TNF; TNF-alpha; a Toll-like receptor agonist (e.g., LPS, muramyl dipeptide, or lipoteichoic acid); GM-CSF; IL-1β; IL-6; IL-12; IL-23, and CD11b.
13. The composition of paragraph 9 or 11, wherein the M2-polarizing agent is selected from the group consisting of:
    IL-4; IL-10; glucocortoids (e.g., cortisol, cortisone, prednisone, prednisolone, methylprednisonolone, dexamethasone, betamethasone, triamcinolone, fludrocortisone acetate, and deoxycorticosterone acetate); M-CSF, TGF-beta, IL-6; and IL-13.
14. The composition of any of paragraphs 1-13, wherein the polymeric particle is substantially discoidal in shape.
15. The composition of paragraph 14, wherein the polymeric particle is discoidal in shape.
16. The composition of any of paragraphs 1-15, wherein the diameter of the polymeric particle is from about 100 nm to about 10 μm.
17. The composition of any of paragraphs 1-15, wherein the diameter of the polymeric particle is from about 100 nm to about 1 μm.
18. The composition of any of paragraphs 1-15, wherein the polymeric particle is about 6 μm×500 nm in size.
19. The composition of any of paragraphs 1-15, wherein the polymeric particle is about 6 μm×250 nm in size.
20. The composition of any of paragraphs 1-15, wherein the polymeric particle is 1-2 μm×7-9 μm in size.
21. The composition of any of paragraphs 1-13, wherein the polymeric particle has a shape which is a cube, a cuboid, a hexahedron, or a pyramid.
22. The composition of any of paragraphs 1-21, wherein the polymeric particle comprises:
    a. a first region comprising one or more cell adhesive molecules (e.g., polyelectrolytes);
    b. a second region comprising one or more structural polymers.
23. The composition of paragraph 22, wherein the cell adhesive molecules comprise one or more of cell adhesive polyelectrolytes, immunoglobulins, or ligands for receptors on monocyte or macrophage cell surfaces.
24. The composition of paragraph 22, wherein the cell adhesive polyelectrolytes comprise hyaluronic acid, hyaluronic acid-aldehyde, and/or poly(allylamine) hydrochloride.
25. The composition of paragraph 24, wherein the hyaluronic acid is modified to comprise aldehyde groups.
26. The composition of any of paragraphs 22-25, wherein the structural polymer comprises poly(lactic-co-glycolic) acid (PLGA), polyvinyl alcohol (PVA), hyaluronic acid (HA), gelatin, collagen or poly(glycerol sebacate) (PGS).
27. The composition of any of paragraphs 22-26, wherein the structural polymer is an 8-12 wt. % solution of the structural polymer.
28. The composition of any of paragraphs 22-27, wherein the structural polymer is a 10 wt. % solution of the structural polymer.
29. The composition of any of paragraphs 22-28, wherein the second region further comprises poly(lactic-co-caprolactone) (PLCL).
30. The composition of any of paragraphs 22-29, wherein the second region comprises or further comprises a near-infrared degradable polymer or polymer linker.

31. The composition of any of paragraphs 22-30 wherein the polymeric particle further comprises one or more monocyte-targeting and/or macrophage-targeting ligands.

32. The composition of paragraph 31, wherein the monocyte-targeting and/or macrophage-targeting ligand is located in the region comprising cell adhesive molecules (e.g., polyelectrolytes).

33. The composition of any of paragraphs 31-32, wherein the monocyte-targeting and/or macrophage-targeting ligand is IgG, an antibody, a polypeptide, or an aptamer.

34. The composition of any of paragraphs 1-33, wherein the polymeric particle further comprises one or more payload molecules.

35. The composition of paragraph 34, wherein the payload molecule is a small molecule or polypeptide.

36. The composition of any of paragraphs 34-35, wherein the payload molecule is present in admixture with the structural polymer.

37. The composition of any of paragraphs 34-36, wherein the payload molecule is present in a third region of the polymeric particle, which is located between the first and second regions.

38. The composition of paragraph 37, wherein the third region further comprises polyvinyl alcohol (PVA).

39. The composition of paragraph 38, wherein the PVA is present at a concentration of less than 1% by weight.

40. The composition of any of paragraphs 1-39, wherein the polymeric particle further comprises an echogenic liposome.

41. The composition of any of paragraphs 1-40, wherein the polymeric particle further comprises a magnetic nanoparticle.

42. The composition of any of paragraphs 1-41, wherein the polymeric particle further comprises a gold nanoparticle.

43. The composition of any of paragraphs 1-42, wherein a region is a layer.

44. The composition of any of paragraphs 1-43, wherein the release of one or more of the polarizing agents is triggered by contacting the particle with a small molecule or nucleic acid.

45. The composition of any of paragraphs 1-44, whereby the phenotype of the macrophage is regulated by the release of the one or more polarizing agents.

46. A method of treating cancer and/or a tumor in a subject in need thereof, the method comprising administering to the subject the engineered cellular composition of any of paragraphs 1-45.

47. The method of paragraph 46, further comprising administering radiation or at least one chemotherapy to the subject.

48. A method of treating a fracture, wound, or infection in a subject in need thereof, the method comprising administering to the subject the engineered cellular composition of any of paragraphs 1-45.

49. A method of treating inflammation in a subject in need thereof, the method comprising administering to the subject the engineered cellular composition of any of paragraphs 1-45.

50. The method of paragraph 49, wherein the inflammation is in the lungs, joints, or skin.

51. The method of any of paragraphs 46-50, wherein the polymeric particle comprises IL-4.

52. The method of any of paragraphs 46-51, wherein the cell is autologous to the subject.

53. The method of any of paragraphs 46-51, wherein the cell is heterologous to the subject.

54. The method of any of paragraphs 46-53, further comprising a first step of obtaining the cell from a donor and/or the subject and contacting the cell with the polymeric particle ex vivo.

55. The method of any of paragraphs 46-54, wherein a therapeutically effective dose of the composition is administered.

56. The method of any of paragraphs 46-55, wherein the second region of the polymeric particle comprises poly(lactic-co-caprolactone) (PLCL) and the method further comprises increasing the temperature of at least one area of the subject in order to permit the cell to phagocytose the polymeric particles.

57. The method of any of paragraphs 46-56, wherein the second region of the polymeric particle comprises a near-infrared degradable polymer or polymer linker and the method further comprises subject at least one area of the subject to near-infrared light in order to permit the cell to phagocytose the polymeric particles.

58. The method of any of paragraphs 46-57, wherein the polymeric particle comprises an echogenic liposome and the method further comprises subject at least one area of the subject to ultrasound in order to permit the cell to phagocytose the polymeric particles or to release a payload molecule.

59. The method of any of paragraphs 46-58, wherein the polymeric particle comprises a magnetic nanoparticle and the method further comprises subject at least one area of the subject to a magnetic field in order to permit the cell to phagocytose the polymeric particles or to release a payload molecule.

60. The method of any of paragraphs 46-59, wherein the polymeric particle comprises a gold nanoparticle and the method further comprises subject at least one area of the subject to an electromagnetic wave in order to permit the cell to phagocytose the polymeric particles or to release a payload molecule.

61. A polymeric particle comprising at least one polarizing agent.

62. The polymeric particle of paragraph 61, wherein the polarizing agent is an M1-polarizing agent.

63. The polymeric particle of paragraph 61, wherein the polarizing agent is an M2-polarizing agent.

64. The polymeric particle of paragraph 61 or 62, wherein the M1-polarizing agent is selected from the group consisting of:
IFN-γ; TNF; TNF-alpha; a Toll-like receptor agonist (e.g., LPS, muramyl dipeptide, or lipoteichoic acid); GM-CSF; IL-1β; IL-6; IL-12; IL-23, and CD11b.

65. The polymeric particle of paragraph 61 or 63, wherein the M2-polarizing agent is selected from the group consisting of:
IL-4; IL-10; glucocortoids (e.g., cortisol, cortisone, prednisone, prednisolone, methylprednisonolone, dexamethasone, betamethasone, triamcinolone, fludrocortisone acetate, and deoxycorticosterone acetate); M-CSF, TGF-beta, IL-6; and IL-13.

66. The polymeric particle of any of paragraphs 61-65, wherein the polymeric particle is substantially discoidal in shape.

67. The polymeric particle of paragraph 66, wherein the polymeric particle is discoidal in shape.

68. The polymeric particle of any of paragraphs 61-67, wherein the diameter of the polymeric particle is from about 100 nm to about 10 μm.

69. The polymeric particle of any of paragraphs 61-67, wherein the diameter of the polymeric particle is from about 100 nm to about 1 µm.
70. The polymeric particle of any of paragraphs 61-67, wherein the polymeric particle is about 6 µm×500 nm in size.
71. The polymeric particle of any of paragraphs 61-67, wherein the polymeric particle is about 6 µm×250 nm in size.
72. The polymeric particle of any of paragraphs 61-67, wherein the polymeric particle is 1-2 µm×7-9 µm in size.
73. The polymeric particle of any of paragraphs 61-65, wherein the polymeric particle has a shape which is a rod, a cylinder, a cube, a cuboid, a hexahedron, or a pyramid.
74. The polymeric particle of any of paragraphs 61-73, wherein the polymeric particle comprises:
    a. a first region comprising one or more cell adhesive molecules (e.g., polyelectrolytes);
    b. a second region comprising one or more structural polymers.
75. The polymeric particle of paragraph 74, wherein the cell adhesive molecules comprise one or more of cell adhesive polyelectrolytes, immunoglobulins, or ligands for receptors on monocyte or macrophage cell surfaces.
76. The polymeric particle of paragraph 75, wherein the cell adhesive polyelectrolytes comprise hyaluronic acid, hyaluronic acid-aldehyde, and/or poly(allylamine) hydrochloride.
77. The polymeric particle of paragraph 76, wherein the hyaluronic acid is modified to comprise aldehyde groups.
78. The polymeric particle of any of paragraphs 74-77, wherein the structural polymer comprises poly(lactic-co-glycolic) acid (PLGA), polyvinyl alcohol (PVA), hyaluronic acid (HA), gelatin, collagen or poly(glycerol sebacate) (PGS).
79. The polymeric particle of any of paragraphs 74-78, wherein the structural polymer is an 8-12 wt. % solution of the structural polymer.
80. The polymeric particle of any of paragraphs 74-79, wherein the structural polymer is a 10 wt. % solution of the structural polymer.
81. The polymeric particle of any of paragraphs 74-80, wherein the second region further comprises poly(lactic-co-caprolactone) (PLCL).
82. The polymeric particle of any of paragraphs 74-81, wherein the second region comprises or further comprises a near-infrared degradable polymer or polymer linker.
83. The polymeric particle of any of paragraphs 74-82, wherein the polymeric particle further comprises one or more monocyte-targeting and/or macrophage-targeting ligands.
84. The polymeric particle of paragraph 83, wherein the monocyte-targeting and/or macrophage-targeting ligand is located in the region comprising cell adhesive molecules (e.g., polyelectrolytes).
85. The polymeric particle of any of paragraphs 83-84, wherein the monocyte-targeting and/or macrophage-targeting ligand is IgG, an antibody, a polypeptide, or an aptamer.
86. The polymeric particle of any of paragraphs 61-85, wherein the polymeric particle further comprises one or more payload molecules.
87. The polymeric particle of paragraph 86, wherein the payload molecule is a small molecule or polypeptide.
88. The polymeric particle of any of paragraphs 86-87, wherein the payload molecule is present in admixture with the structural polymer.
89. The polymeric particle of any of paragraphs 86-88, wherein the payload molecule is present in a third region of the polymeric particle, which is located between the first and second regions.
90. The polymeric particle of paragraph 89, wherein the third region further comprises polyvinyl alcohol (PVA).
91. The polymeric particle of paragraph 90, wherein the PVA is present at a concentration of less than 1% by weight.
92. The polymeric particle of any of paragraphs 61-91, wherein the polymeric particle further comprises an echogenic liposome.
93. The polymeric particle of any of paragraphs 61-92, wherein the polymeric particle further comprises a magnetic nanoparticle.
94. The polymeric particle of any of paragraphs 61-93, wherein the polymeric particle further comprises a gold nanoparticle.
95. The polymeric particle of any of paragraphs 61-94, wherein a region is a layer.
96. The polymeric particle of any of paragraphs 61-95, wherein the release of one or more of the polarizing agents is triggered by contacting the particle with a small molecule or nucleic acid.
97. The polymeric particle of any of paragraphs 61-96, whereby the phenotype of the macrophage is regulated by the release of the one or more polarizing agents.
98. A method of producing a polymeric particle of any of paragraphs 74-97, the method comprising:
    a. applying a layer-by-layer coating of one or more cell adhesive molecules (e.g., polyelectrolytes) to a stamp to form the first region;
    b. applying the one or more structural polymers to the stamp with a spin coater to form the second region;
    c. printing the resulting two regions onto a surface coated with PVA and peeling away the stamp; and
    d. contacting the product of step c with an aqueous solution to release the polymeric particles.
99. A method of producing a polymeric particle of any of paragraphs 89-97, the method comprising:
    a. applying a layer-by-layer coating of one or more cell adhesive molecules (e.g., polyelectrolytes) to a stamp (e.g., with micropatterned features made by soft lithography) to form the first region;
    b. applying the one or more structural polymers to the stamp with a spin coater to form a first layer of the second region;
    c. applying the payload molecule and/or PVA to form the third region;
    d. applying the one or more structural polymers to the stamp with a spin coater to form a second layer of the second region;
    e. printing the product resulting from step d onto a surface coated with PVA and peeling away the stamp; and
    f. contacting the product of step e with an aqueous solution to release the polymeric particles.
100. The method of paragraph 98 or 99, wherein the stamp comprises circular columns.
101. The method of any of paragraphs 98-100, wherein the stamp is a polydimethylsiloxane (PDMS) stamp.

102. The method of any of paragraphs 98-101, wherein the one or more structural polymers are applied as a solution.

103. The method of any of paragraphs 98-102, wherein the one or more structural polymers are applied as a solution in acetone.

104. The method of any of paragraphs 98-103, wherein the PVA on the surface has been previously exposed to water vapor.

EXAMPLES

Example 1: Cellular Backpacks for Adoptive Macrophage Therapy

Adoptive T-cell therapy has shown great promise in treating many cancers, however, its efficacy is contingent on the knowledge and presence of relevant tumor-specific antigens. Adoptive macrophage therapy, on the other hand can mount an antigen-independent anti-cancer response due to its innate immune nature, thus allowing its use for a much wider array of tumors. Previous attempts at translating macrophage-mediated adoptive immunotherapy into the clinic have failed because therapeutic macrophages lose their anti-tumor M1 phenotype once exposed to the tumor microenvironment. Described herein are methods and compositions that overcome this hurdle by attaching a phagocytosis resistant backpack loaded with IFN-γ to the surface of the macrophages. Backpacks provide a depot of IFN-γ to prevent phenotypic shift of macrophages away from an anti-tumor phenotype thus preserving their therapeutic activity. This method provides a practical and clinical solution to address the most significant challenge associated with adoptive macrophage therapies allowing their clinical advancement.

Described herein is a novel adoptive immunotherapy for cancer treatment. Specifically, a novel nanomaterial is provided to control macrophage (MΦ) phenotype to launch an innate attack against cancer in the tumor microenvironment. The nanomaterial is based on a scientific discovery that discoidal polymeric particles (backpacks) attach to the monocytes/macrophages without getting internalized due to their unique shape and flexibility (FIG. 1).[1,2,3] This effect of shape on macrophage response was heralded as a major discovery (Ref 3) and led to the rise of field of shape-engineering of nanoparticles. Monocyte-hitchhiking backpacks can be injected in vivo and they specifically target inflamed tissues.[3].

Attachment of particles without internalization is critical for delivering interferon-γ (IFN-γ) to MΦ surface receptors in a sustained manner. Internalized particles cannot accomplish this task. Backpacks are loaded with IFN-γ to locally control MΦ polarization without causing systemic toxicity, thus achieving a long-term control of MΦ phenotype in the tumor microenvironment. Further, M1 MΦ and correct local cytokine profile enhances the efficacy of checkpoint therapy by providing the necessary help for T cells.

Further described herein are components of the technology including synthesis of backpacks, attachment to monocytes without compromising their survival/differentiation, their trans-endothelial migration, and in vivo ability to target infammation.[1]

In recent years, the field of immunotherapy has produced numerous advances which promise to completely redefine how cancer is treated.[4] Tumors generate sizable degrees of inflammation thereby recruiting large numbers of lymphoid and myeloid cells such as macrophages, up to 50% of the total cell mass, and T-cells.[5] Once incorporated into a tumor, the MΦ's role in determining the disease outcome is highly dependent on their phenotypic polarization into either M1 (pro-inflammatory) or M2 (wound healing/regenerative) type MΦs.[6] Unfortunately, features of tumors such as hypoxia and high rates of apoptosis cause MΦs to adopt an M2 phenotype which is associated with tumor growth and chemotherapy resistance.[7] However, MΦs possessing an M1 phenotype have been demonstrated to be tumoricidal and their presence improves clinical outcome of cancer therapy.[8] The anti-tumor response generated by MΦs has antigen-dependent and -independent facets giving it the potential to be useful in tumors that lack the tumor specific antigens required for adoptive T-cell therapy.[9-11]

Based on these findings, several attempts have been made to clinically translate MΦ-based adoptive immunotherapies.[12-14] Most strategies utilized the general principle of removing and cultivating a patient's peripheral blood monocytes, treating them with an M1-polarizing cytokine, such as IFN-γ, and injecting them back into the patient. Unfortunately, these treatments have been ineffective because the strongly hypoxic nature of the local tumor microenvironment shifts the polarization of the modified MΦs back to an M2 phenotype, even if they have been polarized in vitro; eliminating their therapeutic value. If MΦ adoptive cell therapies are ever to come to fruition, strategies to combat this repolarization need to be developed which allow these cells to resist M2 repolarization by the tumor microenvironment.[8] This is the precise hurdle that our technology will overcome. Specifically, by providing a highly local, sustained delivery of IFN-γ the macrophages can be maintained in the M1 phase for a prolonged time period.

Several key features of backpacks define the functionality of the approach. The shape and flexibility are key features. While the shape of the backpack plays a key role in avoiding their internalization, the flexibility plays an important role in crossing the endothelium. Flexibility can be achieved by reducing the thickness of the backpacks or using soft materials including proteins and biocompatible polymers. Backpacks can be synthesized through several approaches. One of the most promising methods incorporates the use micro-contact printing to design backpacks in a rapid and consistent manner. Described herein is the production of backpacks, which are 6 μm×500 nm disks and can be produced in large quantities in a reproducible fashion. Briefly, a layer-by-layer coating of hyaluronic acid modified to contain aldehyde groups and poly(allylamine) hydrochloride is applied and act as a cell adhesive region (these polyelectrolytes can be switched to whatever is desired) to the surface of a polydimethylsiloxane (PDMS) stamp containing circular columns. A 10 wt. % solution of poly(lactic-co-glycolic) acid (PLGA) containing 1% Rhodamine tagged PLGA in acetone is applied to the surface of the stamp with a spin coater. Once dry, the stamp is printed onto a plastic petri dish coated with a thin layer of poly(vinyl alcohol) (PVA) that has been exposed to hot water vapor. The stamp is peeled away leaving behind the particles. Addition of an aqueous solution to the top of the backpacks causes dissolution of the PVA and particle release.

Backpacks bind with both primary human and mouse monocytes. Studies with mouse monocytes have demonstrated that attachment of backpacks does not hinder the cell's biological function by assessing both viability and endothelial crossing. More importantly, these findings have been extended to primary monocytes. Specifically, it is demonstrated herein that backpacks possess the ability to attach to primary mouse bone marrow monocytes with over 75% efficiency. Monocytes attached to backpacks retained their ability to differentiate into macrophages in response to inflammatory signals. Monocytes also demonstrated the ability to cross endothelial cell layers after attachment to backpacks. Data demonstrate that backpack-carrying monocytes cross endothelium with the same efficiency as native monocytes.

Figure 3:
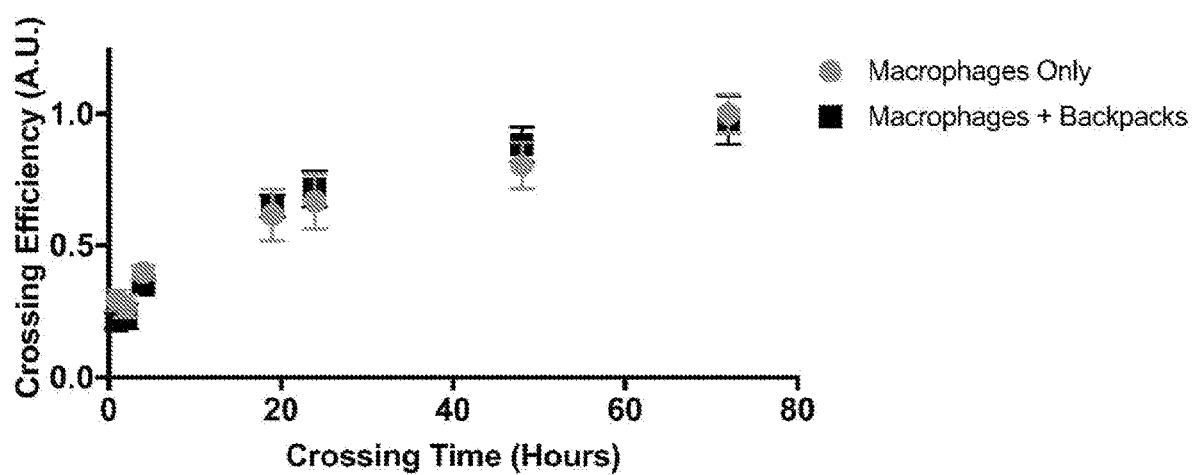
FIG. 3 depicts a graph of penetration of backpack-laden monocytes across the brain endothelial monolayer in response to a cytokine gradient. Backpack-laden monocytes (orange) cross the barrier just as efficiently as unmodified monocytes (blue) indicating that backpacks do not adversely influence monocyte's ability to cross the barrier.

Data in FIG. 3A compares the efficacy of backpack's ability to cross endothelium with and without attachment to monocytes. On their own, backpacks are fairly large and do not cross endothelium. However, when attached to monocytes, backpacks readily cross the endothelium.

Attachment of backpacks to monocytes can be mediated by various factors. In one mode, the polymers used to synthesize backpacks can exhibit affinity for monocytes. This property can be exhibited by hyaluronic acid, which exhibits affinity for CD44 on the surfaces of monocytes. Attachment of backpacks to monocytes can be promoted by incorporation of monocyte-targeting and/or macrophage-targeting ligands. For example, IgG can be used to target Fc receptors on the monocytes.

Payload can be loaded into backpacks in several different ways. For small molecules, the drug will be mixed into the PLGA solution and applied with the PLGA. For application of proteins and other macromolecules, a spray coating or layer-by-layer method can be used to add a layer of active compound to the backpack. Application can be done after the deposition of the initial layer-by-layer region and before the deposition of the PLGA.

The PLGA region of the backpack is used to provide support to the backpack structure. Currently, PLGA is the most commonly used polymer for backpacks however, others exist which can be used as alternatives. Poly(glycerol sebacate) (PGS) is an elastomer that has been shown to be highly flexible and biodegradable. Use of this polymer instead of PLGA would allow backpacks to maintain their strength but also provide them with increased flexibility and more rapid biodegradability. Traditional PGS is set thermally however research has reported modification with acryolyl chloride to allow for UV light as a curing agent, which may help prevent protein degradation.

Backpacks that remain on the surface of macrophages for extended periods of time cause the cells to produce inflammatory signals due to frustrated phagocytosis. The data provided herein indicate that poly(lactic-co-caprolactone) (PLCL) mixed with PLGA produced backpacks which lost their disk structure at body temperature and turned into spheres. Using higher molecular weight of PLCL or reducing the PLCL content can allow particles to undergo a shape change at temperatures slightly higher than what is experienced in the body. When heat is applied, backpacks would change shape allowing for phagocytosis.

External activation can also be used to degrade backpacks to prevent frustrated phagocytosis or allow for controlled release of drugs. Many near infrared light degradable polymers and polymer linkers have been designed for these types of applications. Additionally, liposomes can be added to backpacks. If echogenic liposomes are utilized, drugs can be released via ultrasound.

Additional modalities including magnetic fields or electromagnetic fields. Such modalities require incorporation of additional activators in the backpacks. For example, magnetic nanoparticles can be loaded in the backpacks to promote response to magnetic fields or gold nanoparticles can be incorporated to trigger response to electromagnetic waves. In one modality, the backpack can have multiple modalities to trigger the release of two different drugs in response to two different triggers.

Because particles are relatively flat, the amount of cargo able to be loaded into each is less than monocytes with internalized particles. This means drugs delivered with this method is particularly suited to the delivery of potent drugs. With this in mind, one potential use for this technology is a patch with payload meant to act directly on the carrier cell. Monocytes and Macrophages demonstrate incredible functional diversity from pathogen defense to wound healing largely determined by the signals received by the cell from the local tissue such as damage or pathogen associated molecular patters and cytokines, among others. Many treatments often utilize these signaling molecules to induce a desired response from the immune system. Unfortunately, these compounds effect all types of tissue and thus systemic delivery can have highly undesired side effects at doses that have a therapeutic effect. Cell backpack technology offers a solution for these kinds of therapies by directly localizing the signaling molecules on the target immune cells in high concentration.

As an example, one disease that could show benefit with this treatment is lung inflammation, e.g., acute respiratory distress (ARDS). In a healthy individual, an infection or insult in or near the lungs causes an inflammatory response that dissipates after the infection or insult is resolved. Much of this inflammation is caused in part by polarization of alveolar macrophages to an M1 phenotype while their polarization switches to an M2 phenotype during inflammation resolution. However sometimes, the signaling to resolve the inflammation is not heeded and the macrophages continues to release inflammatory signals. This recruits more monocytes to the lungs forming a positive feedback loop that causes runaway inflammation, e.g., ARDS. While there are currently no treatments specifically for this condition, recent research has indicated that macrophages exposed to IL-4 for 24 h helped resolve inflammation in mouse models. Unfortunately, this disease is characterized by a rapid onset and can cause death in 3-5 days making time an incredibly important factor. Backpacks described above can be loaded with IL-4. Backpacks can be rapidly conjugated to cells in 1-2 h. Once conjugated, macrophages can be injected into the bloodstream and make their way to the lungs. Polarization of macrophages can occur while macrophages are making their way to the lungs instead of having to be done ex vivo. Once in the lungs, IL-4 remaining in the backpacks helps prevent the migrated cells from being repolarized by the inflammation in the lungs. This will give the migrated cells enough time to begin to release anti-inflammatory compounds on their own and switch the lung microenvironment to a healing state.

Adoptive macrophage therapy can also benefit from this technology. Like adoptive T-cell therapy, this treatment modifies immune cells ex vivo so that they will mount an attack on cancerous tissue when reintroduced into the body. Macrophages for this therapy have traditionally been polarized with IFN-γ to induce a strong M1 phenotype. While initially effective, the microenvironment of the tumor often causes repolarization of these cells to be beneficial to tumor growth. Injection of IFN-γ to prevent macrophage reprogramming by macrophages is incredibly dangerous because of the side effects. Backpacks loaded with IFN-γ can be attached to macrophages after their ex-vivo polarization. This would supply a reservoir of IFN-γ to permit the cells to remain polarized. In addition to the specific examples mentioned, macrophage backpacks can also be utilized in many other applications where macrophages are involved including fractures, wounds, infections, etc.

In one modality, blood is drawn from a patient and monocytes are isolated, modified with backpacks, and reintroduced into the blood. Ex vivo isolation prevents clearance of particles by the liver before they are bound to cells. Molecules that have specific and high affinity for monocytes can be designed (peptides, aptamers, antibodies, etc.) this would permit backpacks to be incubated with whole blood which would allow for conjugation to macrophages without having to isolate them from whole blood.

These findings can be adapted to target tumors and modify local tumor microenvironment. Backpacks can overcome the hurdles traditionally associated with adoptive MΦ therapies due to their repolarization upon exposure to the tumor microenvironment. For example, IFN-γ-loaded backpacks can be attached to autologous monocytes for providing a continuous means of polarization control.

Provided herein is an exemplary methodology to synthesize backpacks. Specifically, the backpacks are made completely of biodegradable materials with microcontact printing which is highly consistent and scalable.[15] Particles are cell-compatible and have been shown to successfully traverse the endothelial barrier in vitro when attached to a MΦ. Also provided herein are methods to load cytokines and bioimaging/tracking components into the backpacks. For example, IFN-γ can be loaded in the backpack, providing a cytokine store for the MΦ to draw on deep within the tumor providing continuous M1 stimulation to help prevent M2 repolarization allowing for continuous treatment effectiveness.[16,17]

Example 2

Described herein are four aims that demonstrate the therapeutic efficacy of this approach; (i) IFN-γ can be loaded into the backpacks and its activity and release profile studied. Optimum loading and release rates can be determined, (ii) the effect of backpacks on monocytes can be studied in vitro. Factors (such as the ability of backpacks to maintain M1 polarization in response to tumor cell conditioned media) can be tested by examining gene expression with RT-PCR. Viability of monocytes can be verified. Penetration of backpack-laden monocytes into tumor spheroids can also be tested, (iii) in vivo biodistribution of backpacks can be determined. Monocytes can be modified ex vivo with backpacks and administered to mice. Tumor accumulation of backpacks and off-target distribution can be measured. Toxicity of backpacks themselves can be assessed, (iv) the treatment efficacy of monocyte-backpacks can be tested in vivo using a relevant tumor model where the role of macrophages has been established. Such models have already been developed, e.g., ref 18.

The treatment can be conducted first as a standalone treatment where its therapeutic efficacy is based on the ability of macrophages to shift the tumor microenvironment leading to regression. As an additional approach, the ability of backpack-laden monocytes to serve as a co-therapy with chemotherapeutics and radiation by sensitizing the tumor microenvironment can be assessed. Success of these experiments can be determined by factors such as tumor volume, animal survival time, and levels of expression of various M1 type factors secreted in tumors after treatment incorporation.

REFERENCES FOR EXAMPLES 1 AND 2

1. Anselmo, A. C. et al. Monocyte-mediated delivery of polymeric backpacks to inflamed tissues: a generalized strategy to deliver drugs to treat inflammation. *J. Control. Release* 199, 29-36 (2014).
2. Doshi, N. et al. Cell-based drug delivery devices using phagocytosis-resistant backpacks. *Adv. Mater.* 23, (2011).
3. Champion, J. a & Mitragotri, S. Role of target geometry in phagocytosis. *Proc. Natl. Acad. Sci. U.S.A.* 103, 4930-4934 (2006).
4. Gu, L. & Mooney, D. J. Biomaterials and emerging anticancer therapeutics: Engineering the microenvironment. *Nature Reviews Cancer* 16, 56-66 (2016).
5. Murdoch, C., Giannoudis, A. & Lewis, C. E. Mechanisms regulating the recruitment of macrophages into hypoxic areas of tumors and other ischemic tissues. *Blood* 104, 2224-2234 (2004).
6. Mosser, D. M. & Edwards, J. P. Exploring the full spectrum of macrophage activation. *Nat. Rev. Immunol.* 8, 958-969 (2008).
7. Williams, C. B., Yeh, E. S. & Soloff, A. C. Tumor-associated macrophages: unwitting accomplices in breast cancer malignancy. *npj Breast Cancer* 2, 15025 (2016).
8. Lee, S., Kivimäe, S., Dolor, A. & Szoka, F. C. Macrophage-based cell therapies: The long and winding road. *J. Control. Release* 240, 527-540 (2016).
9. Mills, C. D., Lenz, L. L. & Harris, R. A. A breakthrough: Macrophage-directed cancer immunotherapy. *Cancer Res.* 76, 513-516 (2016).
10. Sullivan, T. O. et al. Cancer immunoediting by the innate immune system in the absence of adaptive immunity. 209, 1869-1882 (2012).
11. Friel, L., Patrick, T. & Declan, F. F. Clinical evaluation of macrophages in cancer: role in treatment, modulation and challenges. *Cancer Immunol. Immunother.* 66, 1509-1527 (2017).
12. Stevenson, H. C. et al. Fate of gamma-interferon-activated killer blood monocytes adoptively transferred into the abdominal cavity of patients with peritoneal carcinomatosis. *Cancer Res.* 47, 6100-6103 (1987).
13. Faradji, A. et al. Phase I trial of intravenous infusion of ex-vivo-activated autologous blood-derived macrophages in patients with non-small-cell lung cancer: Toxicity and immunomodulatory effects. *Cancer Immunol. Immunother.* 33, 319-326 (1991).
14. Hennemann, B., Beckmann, G., Eichelmann, a, Rehm, a & Andreesen, R. Phase I trial of adoptive immunotherapy of cancer patients using monocyte-derived macrophages activated with interferon gamma and lipopolysaccharide. *Cancer Immunol. Immunother.* 45, 250-256 (1998).
15. Wang, Z. et al. Facile functionalization and assembly of live cells with microcontact-printed polymeric biomaterials. *Acta Biomater.* 11, 80-7 (2015).
16. Baer, C. et al. Suppression of microRNA activity amplifies IFN-γ-induced macrophage activation and promotes anti-tumour immunity. *Nat. Cell Biol.* 18, (2016).
17. Long, K. B. et al. IFN-γ and CCL2 cooperate to redirect tumor-infiltrating monocytes to degrade fibrosis and enhance chemotherapy efficacy in pancreatic carcinoma. *Cancer Discov.* 6, 400-413 (2016).
18. Guerriero J L et al., Class IIa HDAC inhibition reduces breast tumours and metastases through anti-tumour macrophages, *Nature*, 453: 429-432,2017.

Example 3

Figure 4:
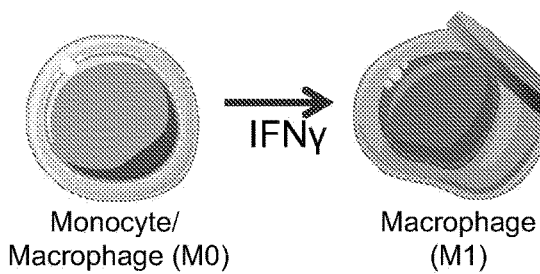
FIG. 4 depicts a schematic of the backpack technology.
Figure 5A:
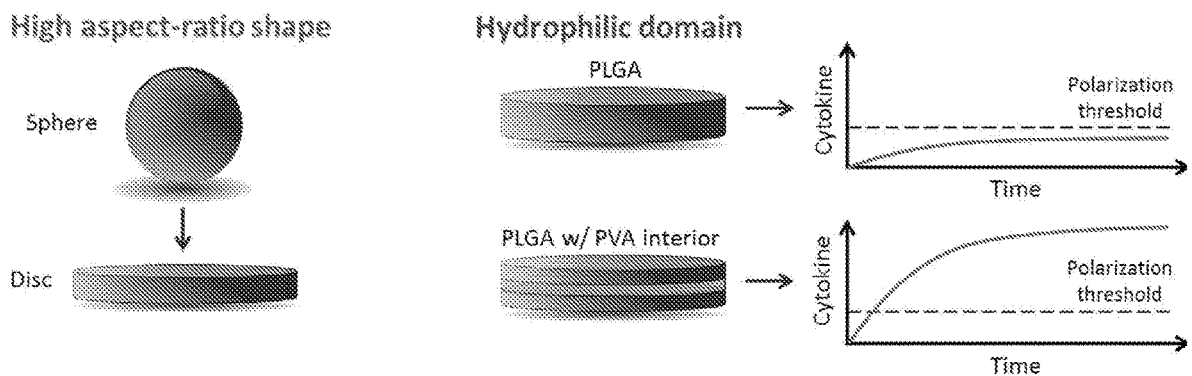
FIGS. 5A-5B depict schematics of backpack design characteristics.
Figure 5B:
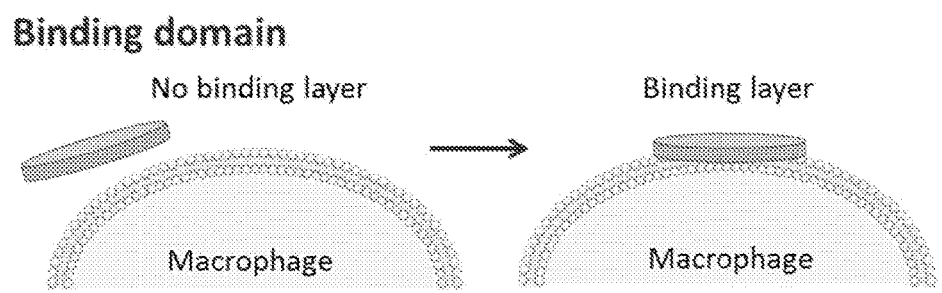

Tumors polarize macrophages toward the M2 phenotype, which is associated with metastasis and death. The technology described herein provides backpacks that bind to macrophages to help them resist this phenotypic shift by encapsulating cytokines that maintain M1 phenotypes (FIG. 4). This provides therapeutic cells in which the backpacks function as a remote control by providing a continuous supply of cytokines. FIGS. 5A-5B depict aspects of the backpack design and their relationship to functional properties.

Figures 6A, 6B, 6C, 6D, 6E, 6F, 6G, 6H, 6I, 6J:
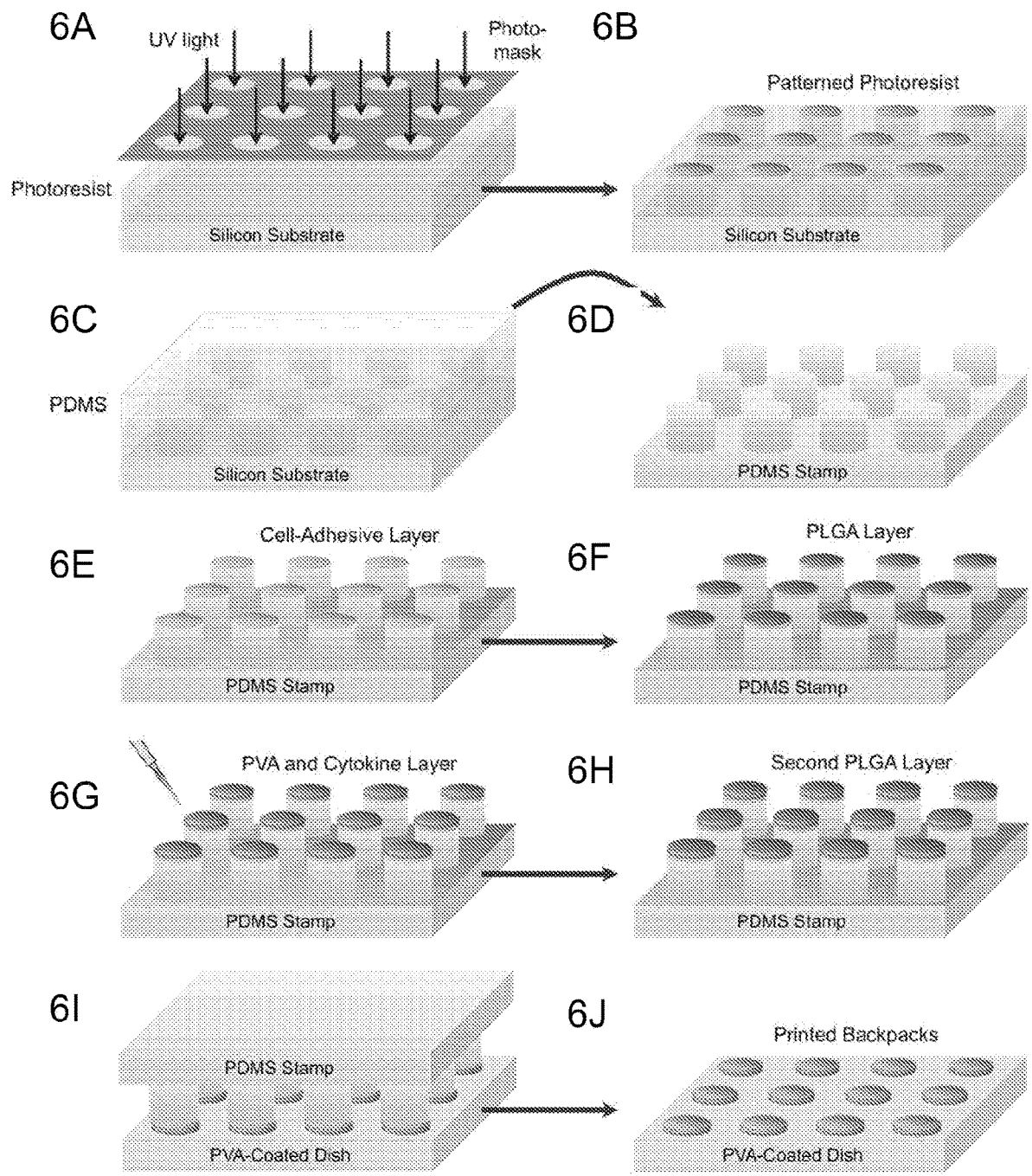
FIGS. 6A-6I depict a schematic of an exemplary backpack production process.

Exemplary production process: Exemplary backpacks can be prepared as follows. A master is prepared via photolithography of SPR 220-7.0 to make 8 µm wide holes (FIG. 6A) and is then coated with fluorinated polymer (FIG. 6B). Polydimethylsiloxane (PDMS) is poured over, degassed, and baked at 65° C. (FIG. 6C). The finished PDMS stamp is peeled off (FIG. 6D). The PDMS stamp is coated with alternating layers of poly(acrylic acid) and poly(allylamine hydrochloride) (FIG. 6E) and PLGA is spin coated onto stamp and plasma ash surface (FIG. 6F). A solution of PVA with cytokine is pipetted onto template surface, then dried in desiccator (FIG. 6G), followed by spin coating of a second layer of PLGA (FIG. 6H). Backpacks are microcontact printed onto PVA-coated Petri-dish that held over a warm bath of water (65° C.) for 15 sec (FIGS. 6I-6J).

Figure 7A:
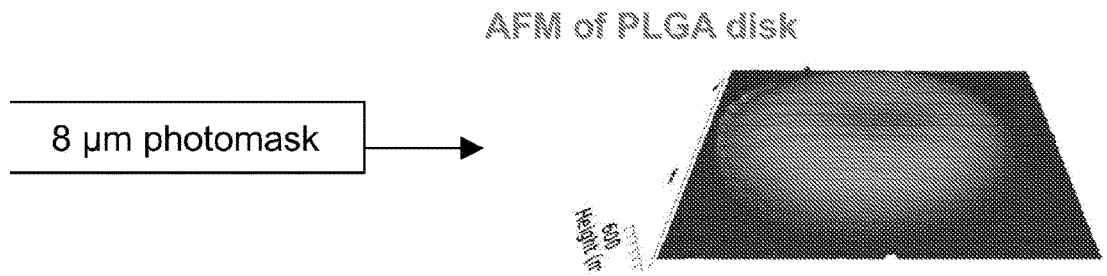
FIGS. 7A-7B depict the characterization of assembled backpacks.
Figure 7B:
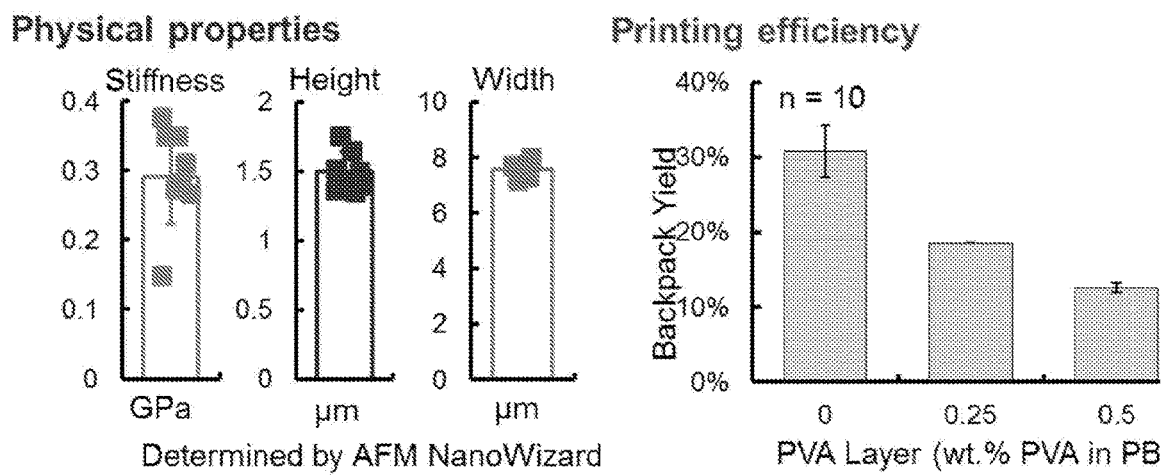
Figure 8:
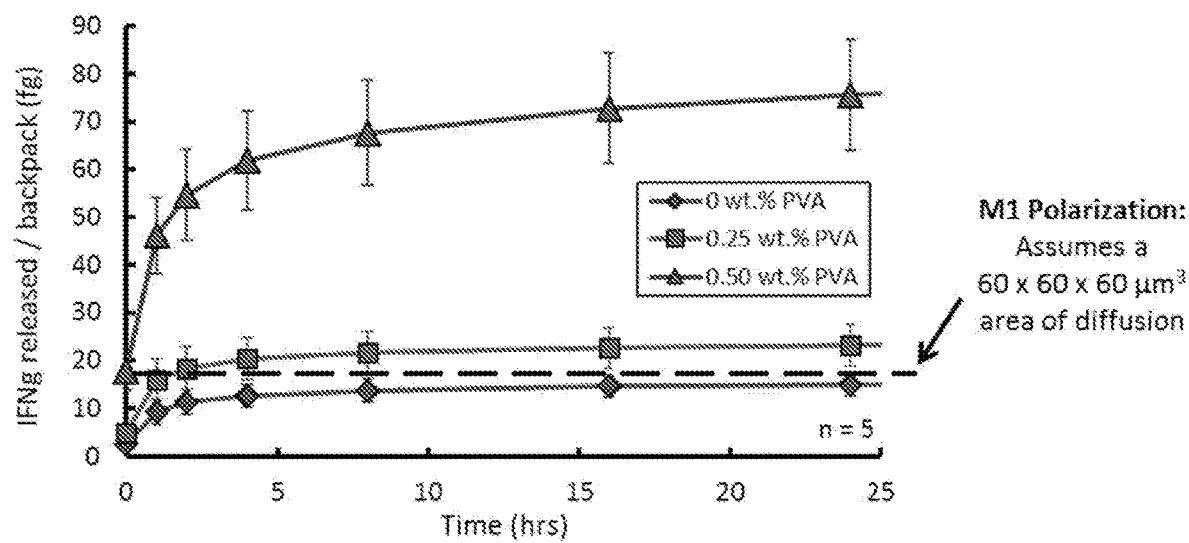
FIG. 8 depicts a graph of cytokine release from backpacks made using the process shown in FIG. 6 over time.
Figure 9:
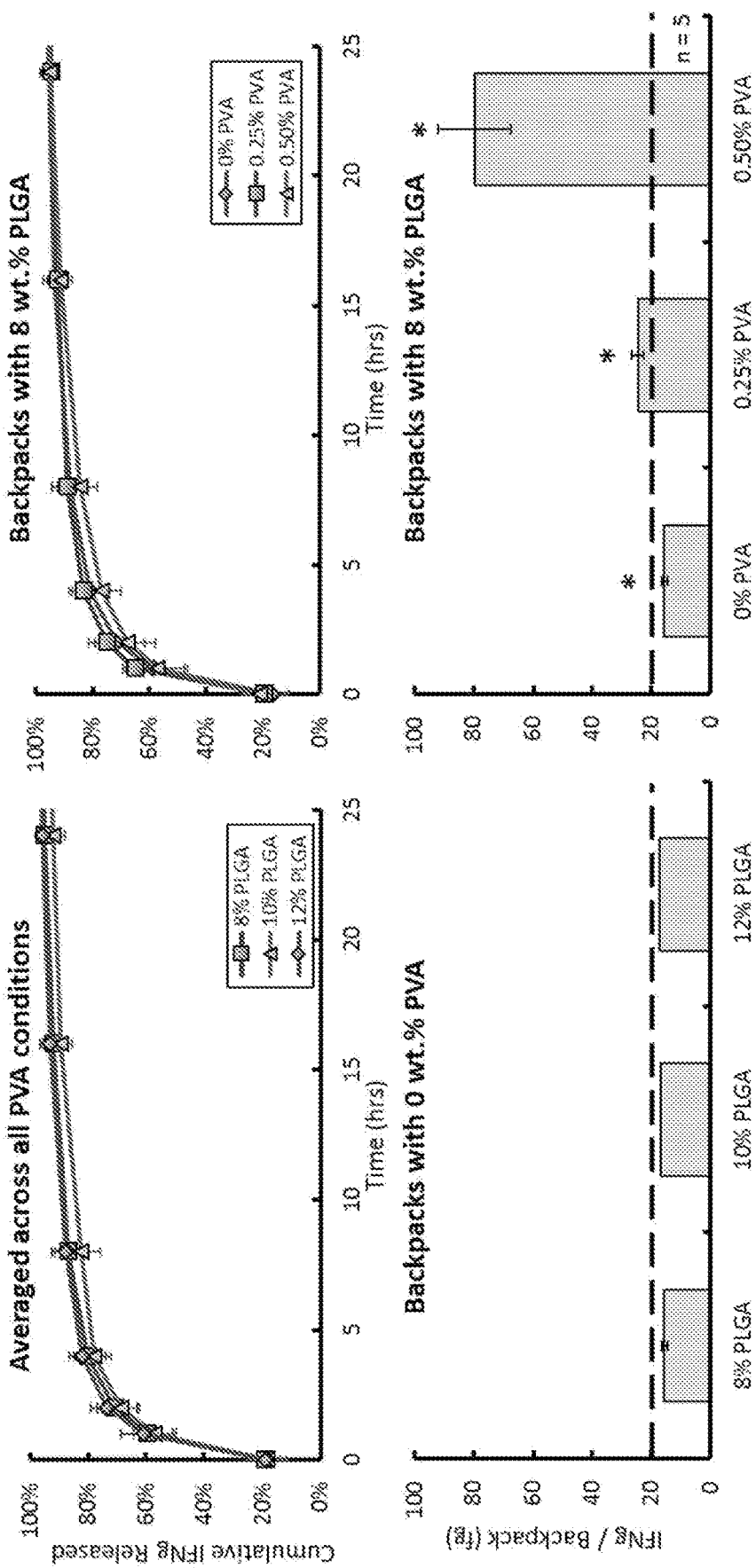
FIG. 9 depicts graphs of cytokine release kinetics for backpacks with the indicated PVA and PLGA layers made using the process shown in FIG. 6.

Assembled backpacks can be assessed for size, physical characteristics, and efficiency (FIGS. 7A-7B). The inclusion of a PVA layer provides ample encapsulation of cytokines, e.g., IFN-γ as demonstrated by the fact that backpacks can stably store cytokines and slowly release those cytokines over 24 hours (FIG. 8). However, the thickness of the PVA and PLGA layers do not appear to mediate the release kinetics, at least within the sizes tested (FIG. 9). Instead, the extent of polymer crosslinking plays a critical role in regulating the release rate of encapsulated cytokine.

Figure 10A:
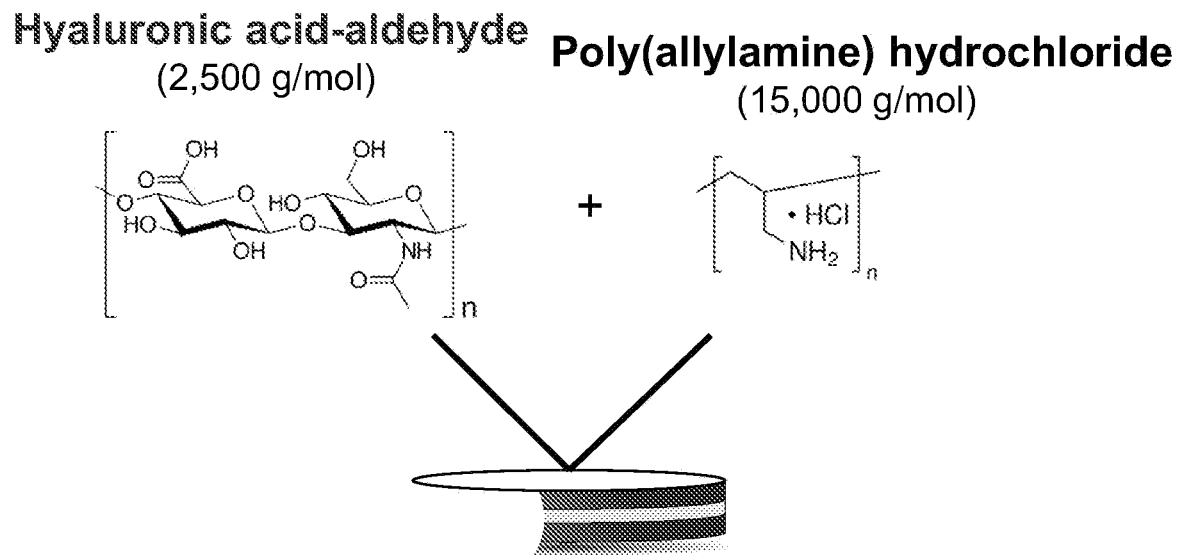
FIG. 10A depicts a schematic of an exemplary attachment layer.
Figure 10B:
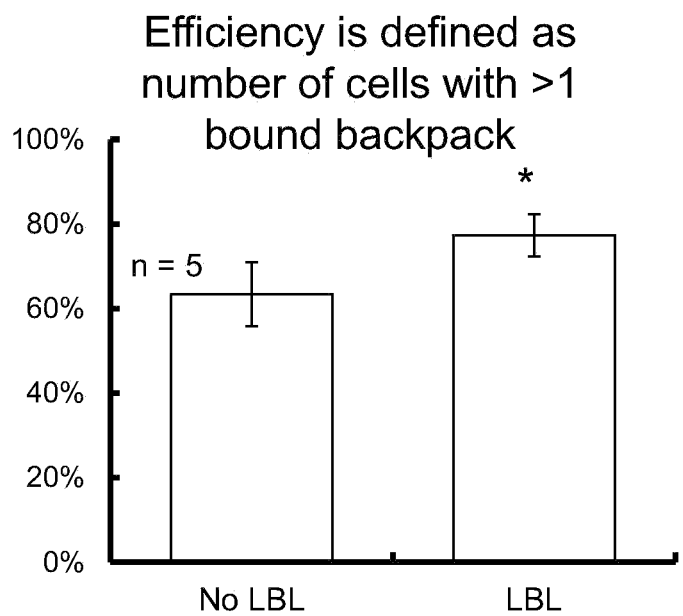
FIG. 10B depicts a graph of backpack attachment efficiency to primary macrophages with and without a layer-by-layer (LBL) film.
Figure 11:
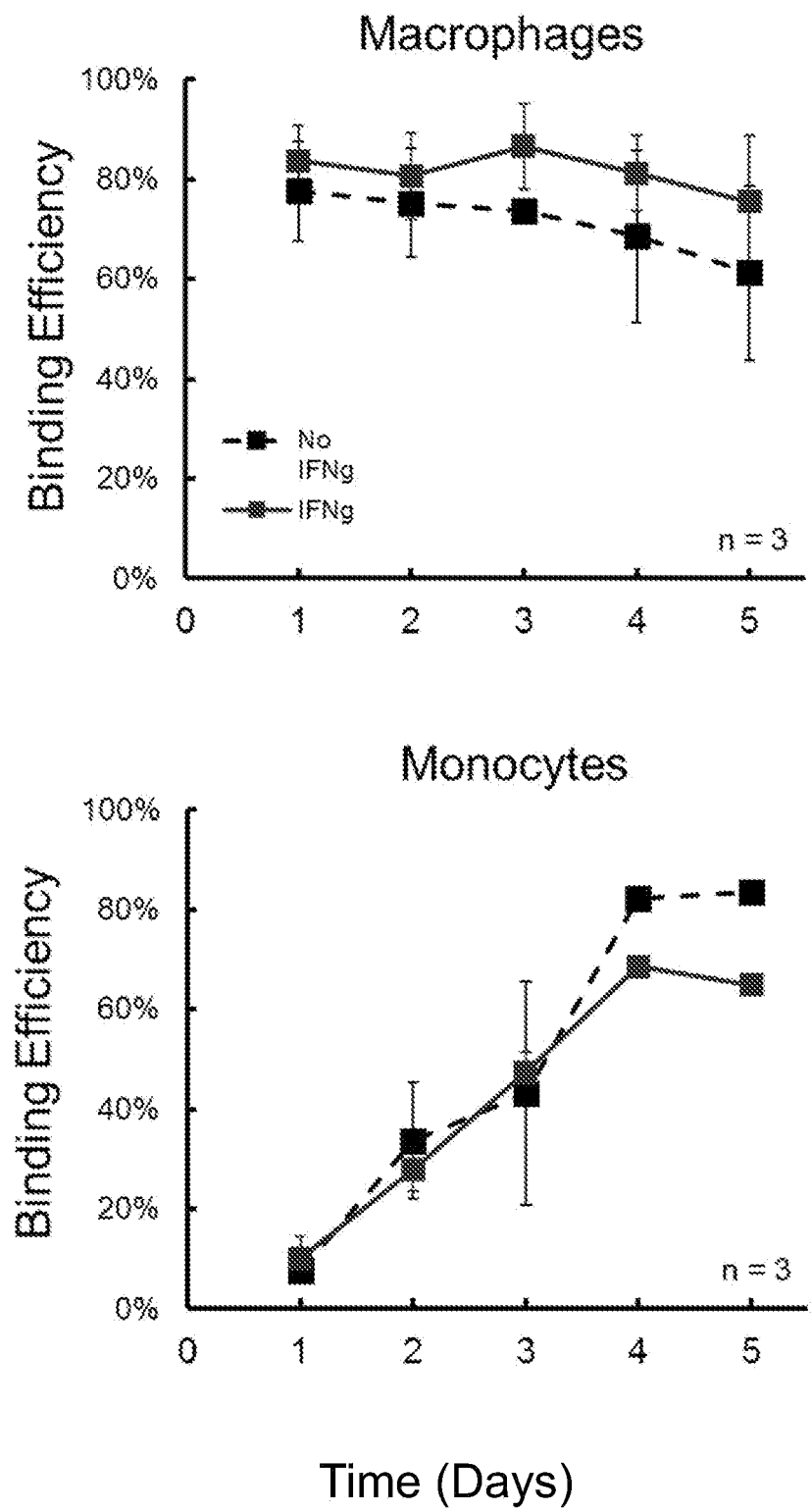
FIG. 11 depicts graphs of backpack binding to the indicated cell types.

Inclusion of an adhesive layer (FIG. 10A) improves attachment of backpacks to macrophages (FIG. 10B). Attachment is improved by using serum-free conditions during the attachment step. Backpack binding to monocytes and macrophages was measured (FIG. 11). Attachment stays fairly constant over time, binding is better when polarized with IFN-γ. Increase in binding over time with monocytes is likely due to their differentiation into macrophages.

Figure 12:
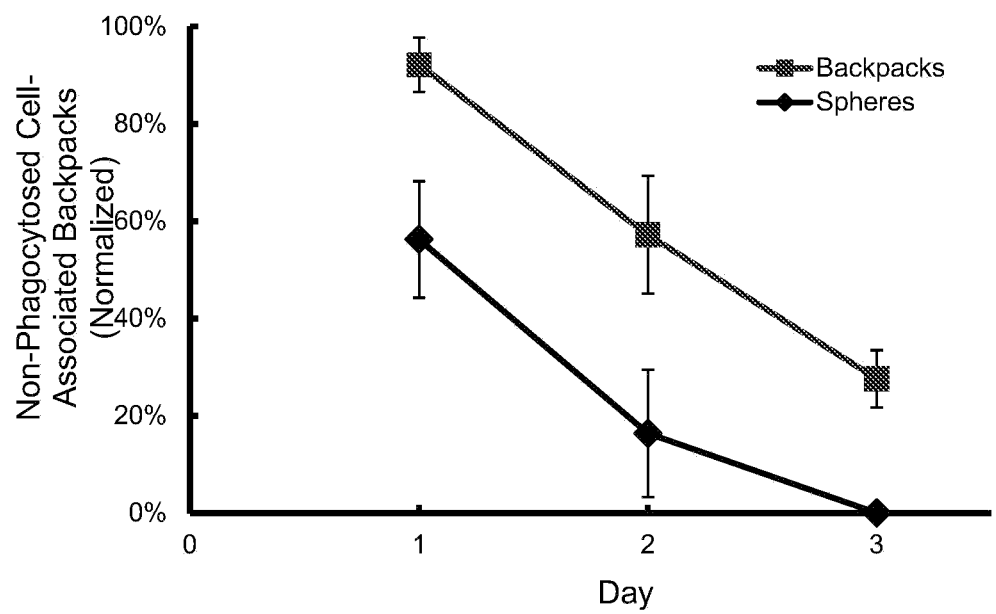
FIG. 12 depicts a graph of the percentage of surface-bound particles NOT phagocytosed.

Discoidal backpacks evade phagocytosis better than spheres (FIG. 12), demonstrating that the anisotropic shape enhances phagocytosis resistance.

Figure 13:
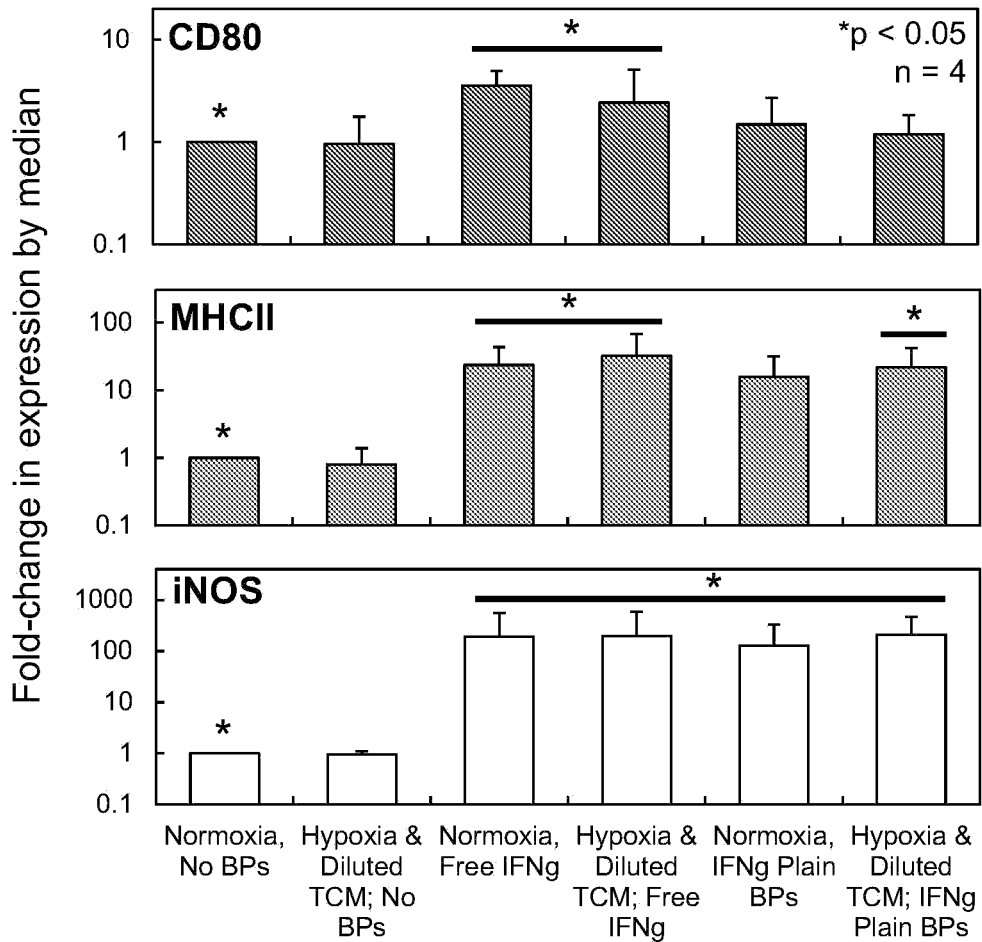
FIG. 13 depicts graphs of M1 marker levels in cells. Markers are—CD80: Co-stimulatory signal for T cells; MHCII: On antigen-presenting cells; iNOS: Used for apoptosis.
Figure 14:
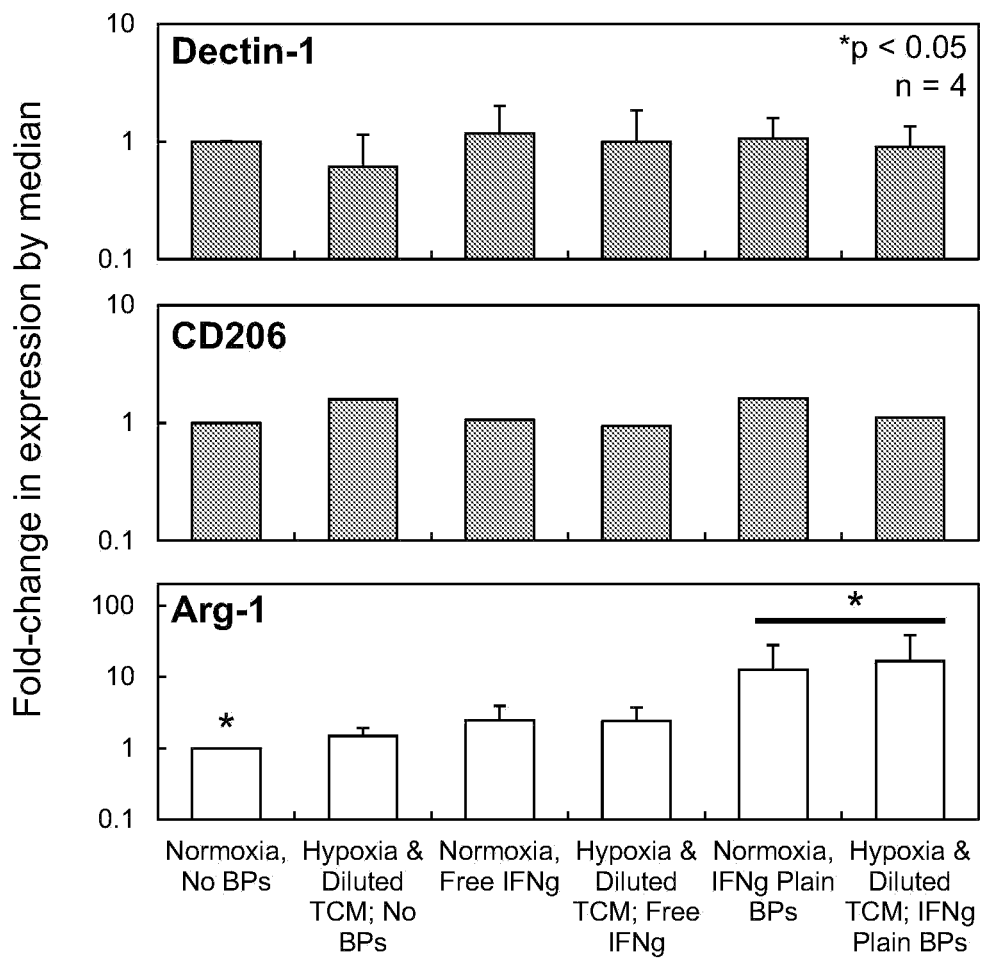
FIG. 14 depicts graphs of M2 marker levels in cells. Markers are—Dectin-1: Highly expressed on tumor-associated macrophages (TAMs); CD206: Mannose receptor, involved in angiogenesis; Arg-1: Involved in urea cycle, implications in wound healing.

The ability of backpacks to polarize macrophages was examined. Flow cytometry studies were conducted by binding backpacks to macrophages via 1.5 hour incubation, washing unbound particles, then incubating for 24 hours in hypoxia (1% $O_2$) and tumor-conditioned media. Cells were then stained for intracellular & surface markers. Backpack-bound cells strongly display key M1 markers after 24 hours (FIG. 13). Conversely, backpacks did not increase M2 markers except for Arg-1 (FIG. 14).

Figures 15A, 15B:
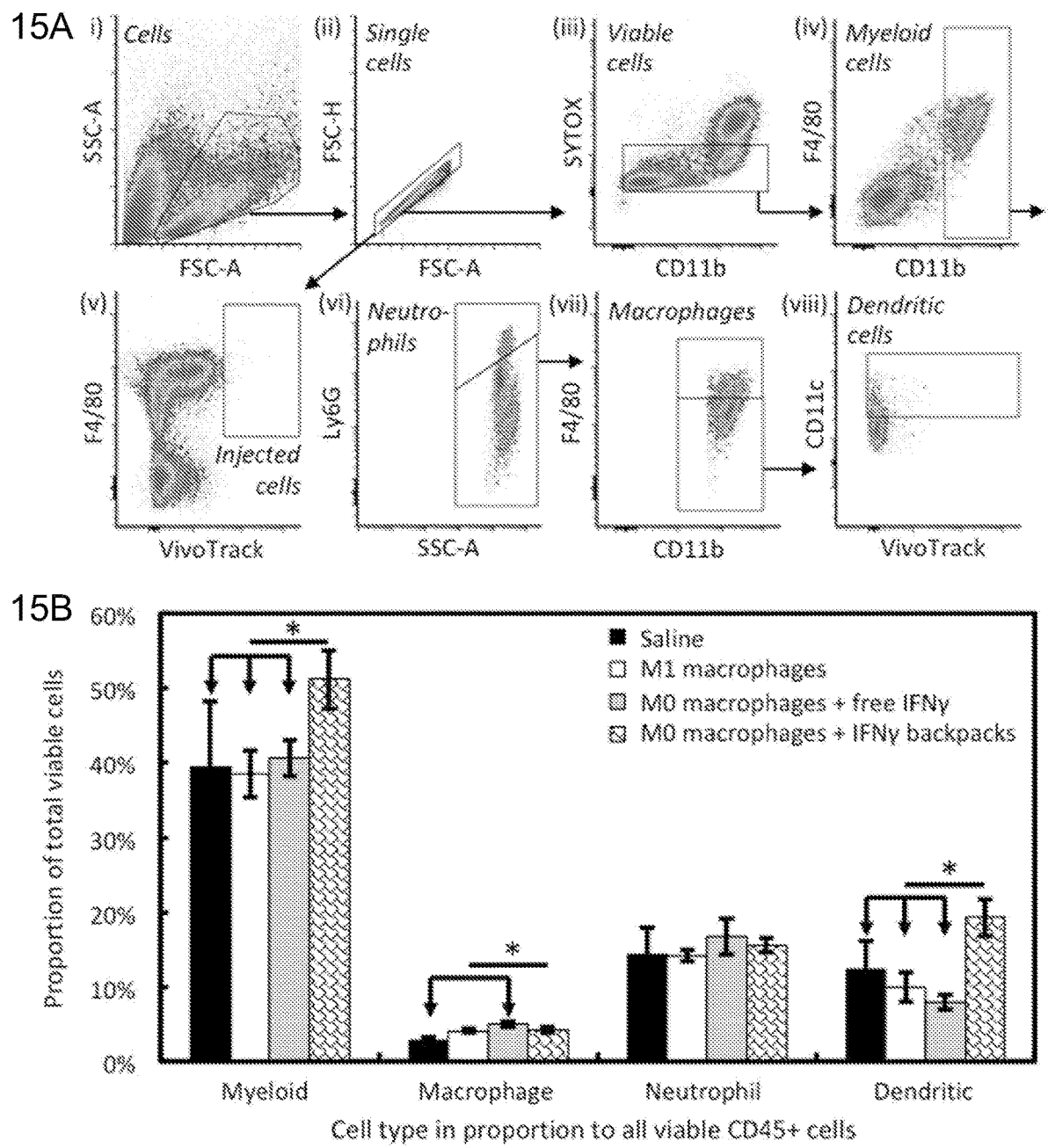
FIGS. 15A-15B depict graphs indicating the levels of cell types in tumors from BALB/c mice inoculated with 4T1 cells (triple-negative breast cancer, TNBC) receiving the indicated treatments.
Figure 16A:
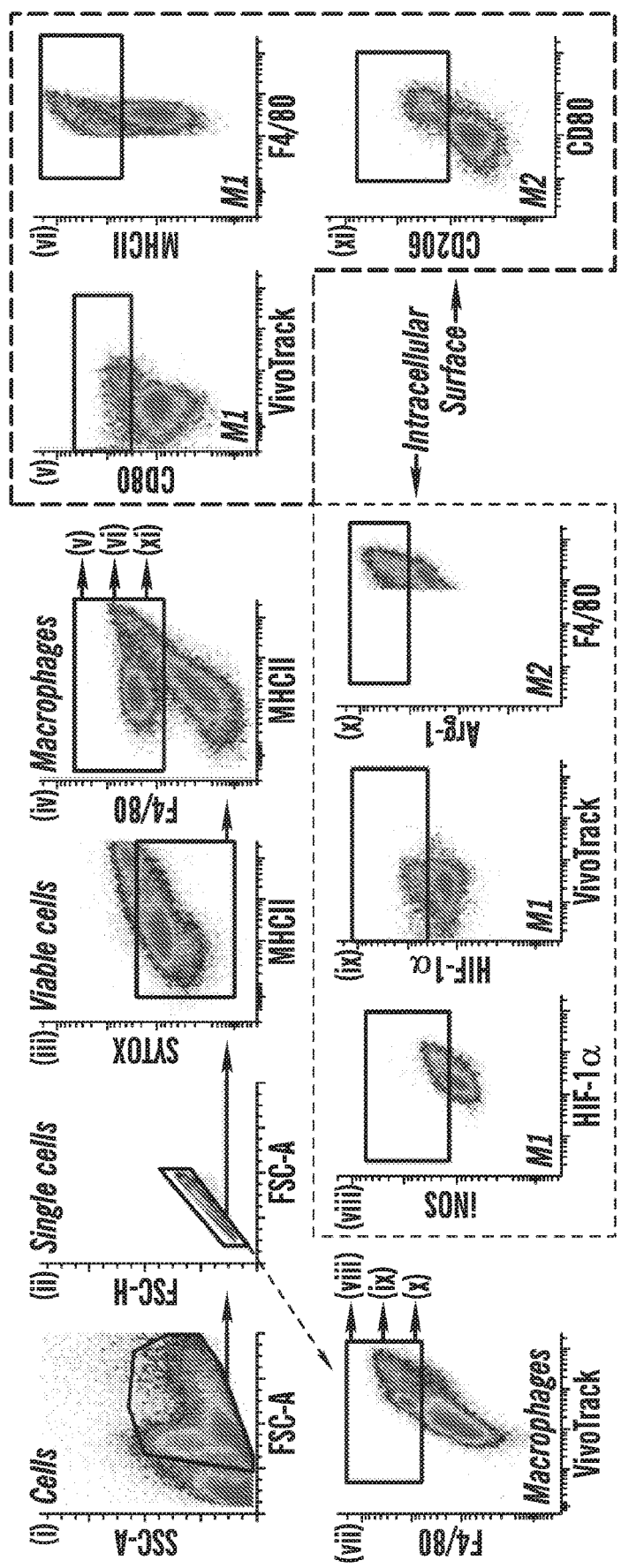
FIGS. 16A-16C depict graphs indicating the phenotypes of cells from the same mice in FIG. 15 (with TNBC) receiving the indicated treatments.
Figure 16C:
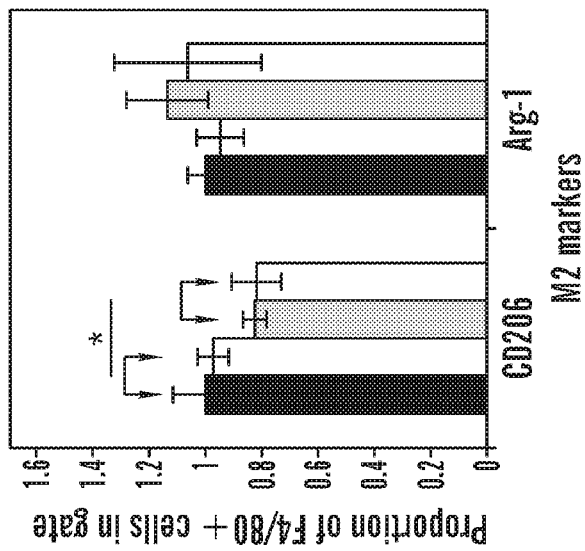
Figure 16B:
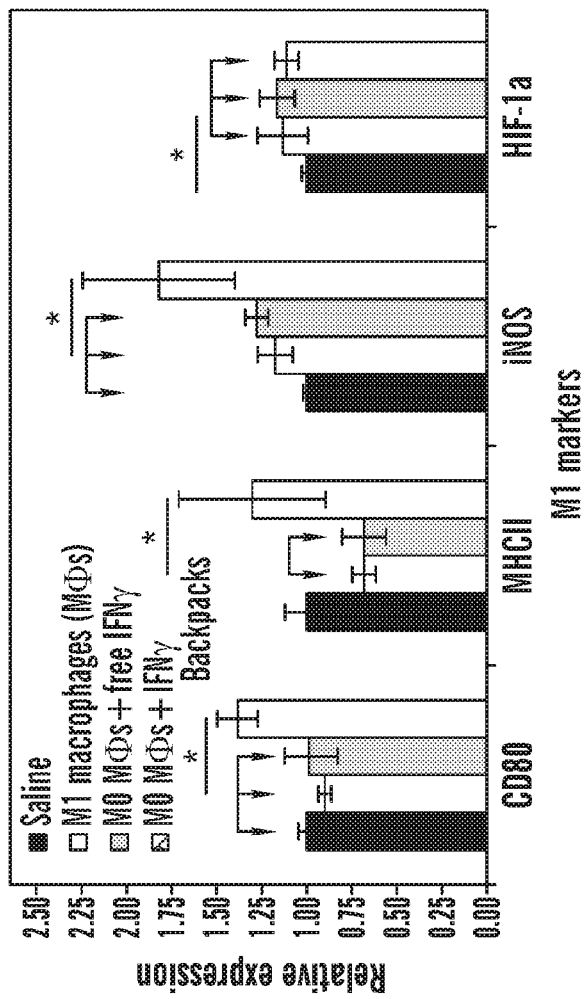

An animal study was conducted in a mouse model of triple negative breast cancer (4T1). The study groups (n=5) were: A. Saline B. Pre-polarized MΦ (24 hrs), no free IFN-γ C. Non-pre-polarized MΦ+50 ng IFN-γ (no backpack), D. Non-pre-polarized MΦ+50 ng IFN-γ loaded into backpacks. The group treated with backpack cells had significantly more dendritic cells, indicating early stages of an adaptive immune response (FIGS. 15A-15B). Additionally, backpack-bound cells maintained an M1 phenotype in tumors (FIGS. 16A-16C). Injected cells with backpacks have significantly higher M2 markers (CD80, MHCII, and iNOS expression) than controls (FIG. 16B). Injected cells with backpacks also have lower CD206 expression (M2 marker) than controls and the same Arg-1 expression (FIG. 16C).

Figure 17:
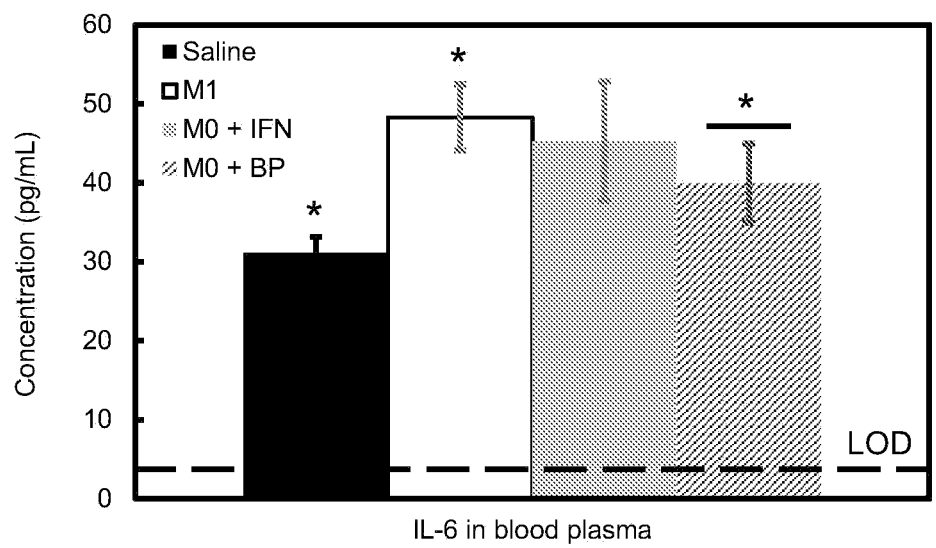
FIG. 17 depicts a graph of IL-6 production in the peripheral blood of the same mice in FIG. 15 (with TNBC) after the injections shown in FIG. 15.

IL-6 is a pro-inflammatory cytokine, has been associated with metastatic cancer. IFN-γ backpacks produce less IL-6 in the blood than free IFN-γ (FIG. 17). The cytokines IL-2, IL-4, IFN-γ, TNF-α, IL-17, and IL-10 were also tested and were below the limit of detection.

Figure 18:
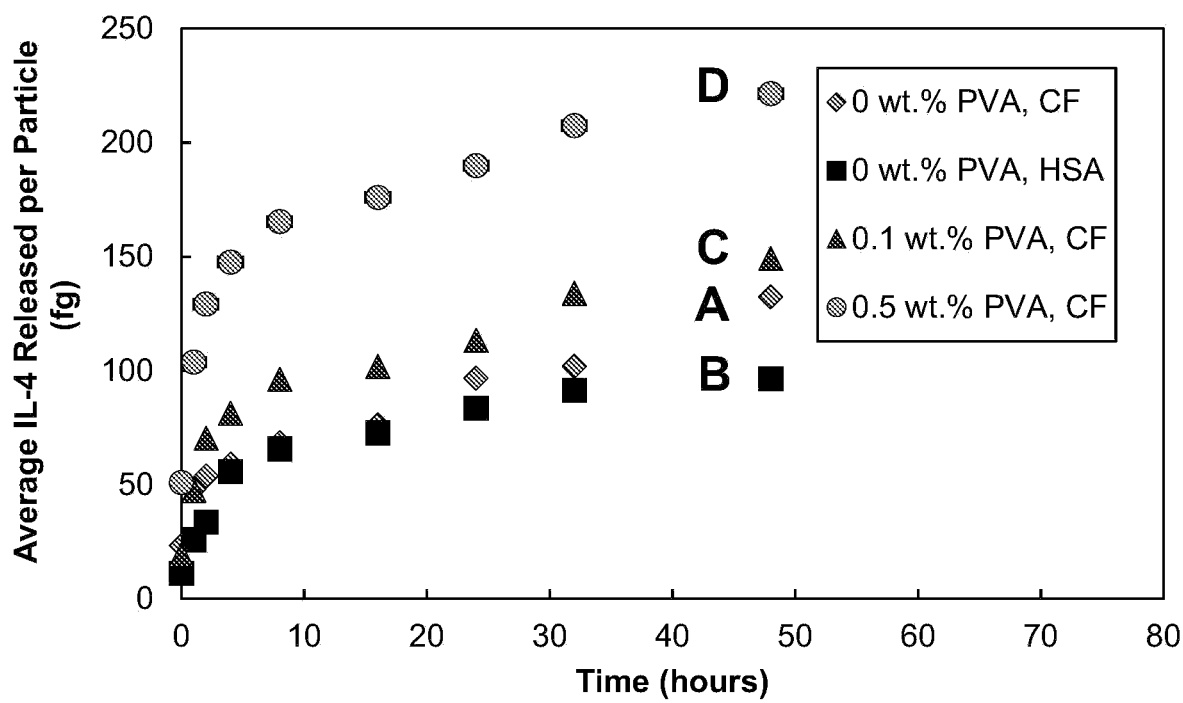
FIG. 18 depicts a graph of IL-4 release from backpacks made using the process shown in FIG. 6 over time.

Backpack cells exhibited sustained IL-4 release (FIG. 18). Calculations indicated that only ~5 fg IL-4 must be present/backpack for activation. Results show that Groups A-D (see FIG. 18) release 20-50× more IL-4 than necessary to polarize macrophages over 48 hours. Data was taken via cumulative measures at each time point (media changed).

What is claimed herein is:

1. A polymeric particle comprising:
   a) a first layer comprising a face of the polymeric particle and:
      i) one or more cell adhesive molecules, the one or more cell adhesive molecules comprising one or more of cell adhesive polyelectrolytes, immunoglobulins, and/or ligands for receptors on monocyte or macrophage cell surfaces; and
      ii) at least one M1-polarizing agent or M2-polarizing agent; and
   b) a second layer comprising one or more structural polymers;
   wherein the diameter of the polymeric particle is from 100 nm to 1 µm.

2. The polymeric particle of claim 1, wherein the M1-polarizing agent is selected from the group consisting of: IFN-γ; TNF; TNF-alpha; a Toll-like receptor agonist; GM-CSF; IL-1β; IL-6; IL-12; IL-23, and CD11b.

3. The polymeric particle of claim 1, wherein the M2-polarizing agent is selected from the group consisting of: IL-4; IL-10; glucocortoids; M-CSF, TGF-beta, IL-6; and IL-13.

4. The polymeric particle of claim 1, wherein the polymeric particle has a shape which is a discoid, a rod, a cylinder, a cube, a cuboid, a hexahedron, or a pyramid.

5. The polymeric particle of claim 1, wherein the cell adhesive polyelectrolytes comprise hyaluronic acid, hyaluronic acid modified to comprise aldehyde groups, hyaluronic acid-aldehyde, and/or poly(allylamine) hydrochloride.

6. The polymeric particle of claim 1, wherein the structural polymer comprises poly(lactic-co-glycolic) acid (PLGA), polyvinyl alcohol (PVA), hyaluronic acid (HA), gelatin, collagen, or poly(glycerol sebacate) (PGS).

7. The polymeric particle of claim 1, wherein the second layer further comprises poly(lactic-co-caprolactone) (PLCL).

8. The polymeric particle of claim 1, wherein the second layer further comprises a near-infrared degradable polymer or polymer linker.

9. The polymeric particle of claim 1, wherein the polymeric particle further comprises one or more monocyte-targeting and/or macrophage-targeting ligands.

10. The polymeric particle of claim 9, wherein the monocyte-targeting and/or macrophage-targeting ligand is located in the first layer.

11. The polymeric particle of claim 9, wherein the monocyte-targeting and/or macrophage-targeting ligand is IgG, an antibody, a polypeptide, or an aptamer.

12. The polymeric particle of claim 1, wherein the polymeric particle further comprises one or more payload molecules.

13. The polymeric particle of claim 12, wherein the payload molecule is present in a third layer of the polymeric particle, which is located between the first and second layers.

14. The polymeric particle of claim 13, wherein the third layer further comprises polyvinyl alcohol (PVA).

15. An engineered cellular composition comprising:
a) a monocyte or macrophage cell; and
b) a polymeric particle comprising:
   i) a first layer comprising a face of the polymeric particle and:
      1) one or more cell adhesive molecules, the one or more cell adhesive molecules comprising one or more of cell adhesive polyelectrolytes, immunoglobulins, and/or ligands for receptors on monocyte or macrophage cell surfaces; and
      2) at least one M1-polarizing agent or M2-polarizing agent; and
   ii) a second layer comprising one or more structural polymers;
wherein the particle is located on the cell surface of the monocyte or macrophage.

16. The composition of claim 15, wherein the macrophage is an M0 macrophage, an M1-polarized macrophage, or an M2-polarized macrophage.

17. A method of treating inflammation, a fracture, a wound, infection, cancer and/or a tumor in a subject in need thereof, the method comprising administering to the subject the engineered cellular composition of claim 15.

18. The polymeric particle of claim 1, wherein only the first layer comprises the M1-polarizing agent or the M2-polarizing agent.

19. The polymeric particle of claim 1, wherein the second layer is formed by spin coating.

20. A polymeric particle comprising:
at least one M1-polarizing agent or M2-polarizing agent;
a first layer comprising one or more cell adhesive molecules on a face of the polymeric particle, the one or more cell adhesive molecules comprising one or more cell adhesive polyelectrolytes; and
a second layer comprising one or more structural polymers, the second layer being formed by spin coating.

21. The polymeric particle of claim 1, wherein the polymeric particle causes a cell it is attached to to assume and retain a M1 phenotype or a M2 phenotype.

* * * * *